(12) United States Patent
Zucherman et al.

(10) Patent No.: US 7,481,840 B2
(45) Date of Patent: Jan. 27, 2009

(54) MULTI-PIECE ARTIFICIAL SPINAL DISK REPLACEMENT DEVICE WITH SELECTABLY POSITIONING ARTICULATING ELEMENT

(75) Inventors: James F. Zucherman, San Francisco, CA (US); Ken Y. Hsu, San Francisco, CA (US)

(73) Assignee: Kyphon Sarl (CH)

( * ) Notice: Subject to any disclaimer, the term of this patent is extended or adjusted under 35 U.S.C. 154(b) by 538 days.

(21) Appl. No.: 10/979,062

(22) Filed: Nov. 2, 2004

(65) Prior Publication Data

US 2006/0069440 A1  Mar. 30, 2006

Related U.S. Application Data

(60) Provisional application No. 60/614,246, filed on Sep. 29, 2004, provisional application No. 60/614,061, filed on Sep. 29, 2004, provisional application No. 60/614,181, filed on Sep. 29, 2004.

(51) Int. Cl.
*A61F 2/44* (2006.01)
(52) U.S. Cl. .................................................. 623/17.15
(58) Field of Classification Search ... 623/17.11–17.16; 606/61
See application file for complete search history.

(56) References Cited

U.S. PATENT DOCUMENTS

| 2,456,806 A | 12/1948 | Wolffe |
| 2,677,369 A | 5/1954 | Knowles |
| 3,426,364 A | 2/1969 | Lumb |
| 3,867,728 A | 2/1975 | Stubstad et al. |
| 3,875,595 A | 4/1975 | Froning |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,636,217 A | 1/1987 | Ogilvie |
| 4,657,550 A | 4/1987 | Daher |
| 4,685,447 A | 8/1987 | Iversen et al. |
| 4,696,290 A | 9/1987 | Steffee |

(Continued)

FOREIGN PATENT DOCUMENTS

CA  2015507  1/1991

(Continued)

OTHER PUBLICATIONS

Tsuji, Haruo, et al., "Ceramic Interspinous Block (CISB) Assisted Anterior Interbody Fusion", Journal of Spinal Disorders, vol. 3, No. 1, pp. 77-86, Raven Press, Ltd., New York (1990).

(Continued)

*Primary Examiner*—Alvin J Stewart
(74) *Attorney, Agent, or Firm*—Haynes and Boone, LLP

(57) ABSTRACT

A posterior approach for intervertebral disk replacement is provided. This technique is particularly suited for assembling a multi-piece artificial spinal disk replacement device in situ in order to alleviate discomfort associated with the spinal column.

26 Claims, 18 Drawing Sheets

U.S. PATENT DOCUMENTS

| | | |
|---|---|---|
| 4,714,469 A | 12/1987 | Kenna |
| 4,743,256 A | 5/1988 | Brantigan |
| 4,759,766 A | 7/1988 | Büttner-Janz et al. |
| 4,759,769 A * | 7/1988 | Hedman et al. .......... 623/17.13 |
| 4,772,287 A | 9/1988 | Ray et al. |
| 4,790,303 A | 12/1988 | Steffee |
| 4,834,757 A | 5/1989 | Brantigan |
| 4,863,477 A | 9/1989 | Monson |
| 4,874,389 A | 10/1989 | Downey |
| 4,878,915 A | 11/1989 | Brantigan |
| 4,904,260 A | 2/1990 | Ray et al. |
| 4,904,261 A | 2/1990 | Dove et al. |
| 4,911,718 A | 3/1990 | Lee et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 4,997,432 A | 3/1991 | Keller |
| 5,002,576 A | 3/1991 | Fuhrmann et al. |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,071,437 A | 12/1991 | Steffee |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,167,662 A | 12/1992 | Hayes et al. |
| 5,171,280 A | 12/1992 | Baumgartner |
| 5,171,281 A | 12/1992 | Parsons et al. |
| 5,180,381 A | 1/1993 | Aust et al. |
| 5,192,326 A | 3/1993 | Bao et al. |
| 5,192,327 A | 3/1993 | Brantigan |
| 5,246,458 A | 9/1993 | Graham |
| 5,258,031 A | 11/1993 | Salib et al. |
| 5,258,043 A | 11/1993 | Stone |
| 5,263,953 A | 11/1993 | Bagby |
| 5,290,312 A | 3/1994 | Kojimoto et al. |
| 5,306,307 A | 4/1994 | Senter |
| 5,306,308 A | 4/1994 | Gross et al. |
| 5,306,309 A | 4/1994 | Wagner et al. |
| 5,313,962 A | 5/1994 | Obenchain |
| 5,314,477 A | 5/1994 | Marnay |
| 5,314,478 A | 5/1994 | Oka et al. |
| 5,320,644 A | 6/1994 | Baumgartner |
| 5,336,223 A | 8/1994 | Rogers |
| 5,350,397 A | 9/1994 | Palermo et al. |
| 5,354,302 A | 10/1994 | Ko |
| 5,360,430 A | 11/1994 | Lin |
| 5,366,508 A | 11/1994 | Brekke |
| 5,370,693 A | 12/1994 | Kelman et al. |
| 5,370,697 A | 12/1994 | Baumgartner |
| 5,375,823 A | 12/1994 | Navas |
| 5,383,884 A | 1/1995 | Summers |
| 5,390,683 A | 2/1995 | Pisharodi |
| 5,395,317 A | 3/1995 | Kambin |
| 5,395,372 A | 3/1995 | Holt et al. |
| 5,397,364 A | 3/1995 | Kozak et al. |
| 5,401,269 A | 3/1995 | Büttner-Janz et al. |
| 5,415,704 A | 5/1995 | Davidson |
| 5,423,816 A | 6/1995 | Lin |
| 5,423,817 A | 6/1995 | Lin |
| 5,425,772 A | 6/1995 | Brantigan |
| 5,425,773 A | 6/1995 | Boyd et al. |
| 5,425,777 A | 6/1995 | Sarkisian et al. |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,456,722 A | 10/1995 | McLeod et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,480,401 A | 1/1996 | Navas |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,505,732 A * | 4/1996 | Michelson .................. 606/61 |
| 5,507,816 A | 4/1996 | Bullivant |
| 5,514,180 A | 5/1996 | Heggeness et al. |
| 5,522,899 A | 6/1996 | Michelson |
| 5,531,793 A | 7/1996 | Kelman et al. |
| 5,534,023 A | 7/1996 | Henley |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,540,689 A | 7/1996 | Sanders et al. |
| 5,545,229 A | 8/1996 | Parsons et al. |
| 5,549,679 A | 8/1996 | Kuslich |
| 5,554,191 A | 9/1996 | Lahille et al. |
| 5,556,431 A | 9/1996 | Büttner-Janz |
| 5,562,736 A * | 10/1996 | Ray et al. .................. 606/61 |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,571,192 A | 11/1996 | Schönhöffer |
| 5,591,235 A | 1/1997 | Kuslich |
| 5,593,409 A | 1/1997 | Michelson |
| 5,599,279 A | 2/1997 | Slotman et al. |
| 5,601,556 A | 2/1997 | Pisharodi |
| 5,603,713 A | 2/1997 | Aust et al. |
| 5,609,634 A | 3/1997 | Voydeville |
| 5,609,635 A | 3/1997 | Michelson |
| 5,609,636 A | 3/1997 | Kohrs et al. |
| 5,620,458 A | 4/1997 | Green et al. |
| 5,645,592 A | 7/1997 | Nicolais et al. |
| 5,645,596 A | 7/1997 | Kim et al. |
| 5,645,597 A | 7/1997 | Krapiva |
| 5,645,598 A * | 7/1997 | Brosnahan, III ............. 606/61 |
| 5,653,761 A | 8/1997 | Pisharodi |
| 5,653,762 A | 8/1997 | Pisharodi |
| 5,658,335 A | 8/1997 | Allen |
| 5,658,336 A | 8/1997 | Pisharodi |
| 5,658,337 A | 8/1997 | Kohrs et al. |
| 5,669,909 A | 9/1997 | Zdeblick et al. |
| 5,674,294 A | 10/1997 | Bainville et al. |
| 5,674,295 A * | 10/1997 | Ray et al. ................ 623/17.12 |
| 5,674,296 A | 10/1997 | Bryan et al. |
| 5,676,701 A | 10/1997 | Yuan et al. |
| 5,676,702 A | 10/1997 | Ratron |
| 5,683,463 A | 11/1997 | Godefroy et al. |
| 5,683,464 A | 11/1997 | Wagner et al. |
| 5,683,465 A | 11/1997 | Shinn et al. |
| 5,693,100 A | 12/1997 | Pisharodi |
| 5,697,889 A | 12/1997 | Slotman et al. |
| 5,697,977 A | 12/1997 | Pisharodi |
| 5,700,292 A * | 12/1997 | Margulies .................. 606/61 |
| 5,702,449 A | 12/1997 | McKay |
| 5,702,450 A | 12/1997 | Bisserie |
| 5,702,454 A * | 12/1997 | Baumgartner ............... 128/898 |
| 5,702,455 A | 12/1997 | Saggar |
| 5,716,415 A * | 2/1998 | Steffee .................... 623/17.16 |
| 5,716,416 A | 2/1998 | Lin |

| | | | | | | |
|---|---|---|---|---|---|---|
| 5,741,253 | A | 4/1998 | Michelson | 6,111,164 A | 8/2000 | Rainey et al. |
| 5,755,732 | A | 5/1998 | Green et al. | 6,113,637 A | 9/2000 | Gill et al. |
| 5,755,796 | A | 5/1998 | Ibo et al. | 6,113,638 A | 9/2000 | Williams et al. |
| 5,755,798 | A | 5/1998 | Papavero et al. | 6,113,639 A | 9/2000 | Ray et al. |
| 5,766,252 | A | 6/1998 | Henry et al. | 6,120,502 A | 9/2000 | Michelson |
| 5,772,661 | A | 6/1998 | Michelson | 6,120,503 A | 9/2000 | Michelson |
| 5,776,196 | A | 7/1998 | Matsuzaki et al. | 6,123,705 A | 9/2000 | Michelson |
| 5,776,199 | A | 7/1998 | Michelson | 6,126,689 A | 10/2000 | Brett |
| 5,782,830 | A | 7/1998 | Farris | 6,127,597 A | 10/2000 | Beyar et al. |
| 5,782,832 | A | 7/1998 | Larsen et al. | 6,129,763 A | 10/2000 | Chauvin et al. |
| 5,782,919 | A | 7/1998 | Zdeblick et al. | 6,132,430 A | 10/2000 | Wagner |
| 5,797,909 | A | 8/1998 | Michelson | 6,132,465 A | 10/2000 | Ray et al. |
| 5,800,438 | A | 9/1998 | Tuke et al. | 6,136,001 A | 10/2000 | Michelson |
| 5,800,550 | A | 9/1998 | Sertich | 6,136,031 A | 10/2000 | Middleton |
| 5,824,093 | A | 10/1998 | Ray et al. | 6,139,579 A | 10/2000 | Steffee et al. |
| 5,824,094 | A | 10/1998 | Serhan et al. | 6,146,421 A | 11/2000 | Gordon et al. |
| 5,827,328 | A | 10/1998 | Buttermann | 6,146,422 A | 11/2000 | Lawson |
| 5,836,948 | A | 11/1998 | Zuckerman et al. | 6,149,650 A | 11/2000 | Michelson |
| 5,860,973 | A | 1/1999 | Michelson | 6,149,652 A | 11/2000 | Zucherman et al. |
| 5,860,977 | A | 1/1999 | Zucherman et al. | 6,149,686 A | 11/2000 | Kuslich et al. |
| 5,865,845 | A | 2/1999 | Thalgott | 6,152,926 A | 11/2000 | Zucherman et al. |
| 5,865,846 | A | 2/1999 | Bryan et al. | 6,156,038 A | 12/2000 | Zuckerman et al. |
| 5,876,404 | A | 3/1999 | Zuckerman et al. | 6,156,067 A | 12/2000 | Bryan et al. |
| 5,885,292 | A | 3/1999 | Moskovitz et al. | 6,159,215 A | 12/2000 | Urbahns et al. |
| 5,885,299 | A | 3/1999 | Winslow et al. | 6,162,252 A | 12/2000 | Kuras et al. |
| 5,888,222 | A | 3/1999 | Coates et al. | 6,165,218 A | 12/2000 | Husson et al. |
| 5,888,224 | A | 3/1999 | Beckers et al. | 6,176,882 B1 | 1/2001 | Biedermann et al. |
| 5,888,226 | A | 3/1999 | Rogozinski | 6,179,874 B1 | 1/2001 | Cauthen |
| 5,888,227 | A | 3/1999 | Cottle | 6,183,471 B1 | 2/2001 | Zucherman et al. |
| 5,891,147 | A | 4/1999 | Moskovitz et al. | 6,190,387 B1 | 2/2001 | Zucherman et al. |
| 5,893,889 | A | 4/1999 | Harrington | 6,190,414 B1 | 2/2001 | Young et al. |
| 5,893,890 | A | 4/1999 | Pisharodi | 6,193,757 B1 | 2/2001 | Foley et al. |
| 5,895,426 | A | 4/1999 | Scarborough et al. | 6,206,922 B1 * | 3/2001 | Zdeblick et al. ......... 623/17.11 |
| 5,895,427 | A | 4/1999 | Kuslich et al. | 6,210,412 B1 * | 4/2001 | Michelson ................. 606/61 |
| 5,895,428 | A | 4/1999 | Berry | 6,224,595 B1 | 5/2001 | Michelson |
| 5,899,941 | A | 5/1999 | Nishijima et al. | 6,224,607 B1 | 5/2001 | Michelson |
| 5,906,616 | A | 5/1999 | Pavlov et al. | 6,224,631 B1 | 5/2001 | Kohrs |
| 5,919,235 | A | 7/1999 | Husson et al. | 6,228,118 B1 | 5/2001 | Gordon |
| 5,928,284 | A | 7/1999 | Mehdizadeh | 6,231,609 B1 | 5/2001 | Mehdizadeh |
| 5,944,754 | A | 8/1999 | Vacanti | 6,234,705 B1 | 5/2001 | Troxell |
| 5,945,115 | A | 8/1999 | Dunn et al. | 6,235,030 B1 | 5/2001 | Zucherman et al. |
| 5,961,554 | A | 10/1999 | Jamson et al. | 6,238,397 B1 | 5/2001 | Zucherman et al. |
| 5,964,807 | A | 10/1999 | Gan et al. | 6,241,769 B1 | 6/2001 | Nicholson et al. |
| 5,976,186 | A | 11/1999 | Bao et al. | 6,241,770 B1 | 6/2001 | Michelson |
| 5,980,572 | A | 11/1999 | Kim et al. | 6,241,771 B1 | 6/2001 | Gresser et al. |
| 5,984,967 | A | 11/1999 | Zdeblick et al. | 6,245,072 B1 | 6/2001 | Zdeblick et al. |
| 5,989,291 | A | 11/1999 | Ralph et al. | 6,245,108 B1 | 6/2001 | Biscup |
| 6,001,130 | A | 12/1999 | Bryan et al. | 6,258,125 B1 | 7/2001 | Paul et al. |
| 6,004,573 | A | 12/1999 | Rathi et al. | 6,261,296 B1 | 7/2001 | Aebi et al. |
| 6,005,162 | A | 12/1999 | Constantz | 6,264,655 B1 | 7/2001 | Pisharodi |
| 6,019,792 | A | 2/2000 | Cauthen | 6,264,656 B1 | 7/2001 | Michelson |
| 6,019,793 | A | 2/2000 | Perren et al. | 6,264,695 B1 | 7/2001 | Stoy |
| 6,022,376 | A | 2/2000 | Assell et al. | 6,270,498 B1 | 8/2001 | Michelson |
| 6,039,761 | A | 3/2000 | Li et al. | 6,277,149 B1 | 8/2001 | Boyle et al. |
| 6,039,763 | A | 3/2000 | Shelokov | 6,280,444 B1 | 8/2001 | Zucherman et al. |
| 6,042,582 | A | 3/2000 | Ray | 6,280,475 B1 | 8/2001 | Bao et al. |
| 6,045,579 | A | 4/2000 | Hochshuler et al. | 6,287,343 B1 | 9/2001 | Kuslich et al. |
| 6,045,580 | A | 4/2000 | Scarborough et al. | 6,290,724 B1 | 9/2001 | Marino |
| 6,048,342 | A | 4/2000 | Zucherman et al. | 6,296,664 B1 | 10/2001 | Middleton |
| 6,051,648 | A | 4/2000 | Rhee et al. | 6,296,665 B1 | 10/2001 | Strnad et al. |
| 6,068,630 | A | 5/2000 | Zucherman et al. | 6,302,914 B1 | 10/2001 | Michelson |
| 6,074,390 | A | 6/2000 | Zucherman et al. | 6,309,421 B1 | 10/2001 | Pisharodi |
| 6,080,155 | A | 6/2000 | Michelson | 6,311,562 B1 | 11/2001 | Hanada |
| 6,080,158 | A | 6/2000 | Lin | 6,315,795 B1 | 11/2001 | Scarborough et al. |
| 6,080,193 | A | 6/2000 | Hochshuler et al. | 6,315,797 B1 | 11/2001 | Middleton |
| 6,086,613 | A | 7/2000 | Camino et al. | 6,325,827 B1 | 12/2001 | Lin |
| 6,090,112 | A | 7/2000 | Zucherman et al. | 6,332,882 B1 | 12/2001 | Zucherman et al. |
| 6,093,205 | A | 7/2000 | McLeod et al. | 6,332,883 B1 | 12/2001 | Zucherman et al. |
| 6,096,038 | A | 8/2000 | Michelson | 6,332,894 B1 | 12/2001 | Stalcup et al. |
| 6,096,080 | A | 8/2000 | Nicholson et al. | 6,342,074 B1 | 1/2002 | Simpson |
| 6,099,531 | A | 8/2000 | Bonutti | 6,348,071 B1 | 2/2002 | Steffee et al. |
| 6,102,950 | A | 8/2000 | Vaccaro | 6,350,283 B1 | 2/2002 | Michelson |
| 6,110,210 | A | 8/2000 | Norton et al. | 6,364,880 B1 | 4/2002 | Michelson |

| | | |
|---|---|---|
| 6,368,350 B1 | 4/2002 | Erickson et al. |
| 6,368,351 B1 | 4/2002 | Glenn et al. |
| 6,371,984 B1 | 4/2002 | Van Dyke et al. |
| 6,371,988 B1 | 4/2002 | Pafford et al. |
| 6,371,989 B1 | 4/2002 | Chauvin et al. |
| 6,379,355 B1 | 4/2002 | Zucherman et al. |
| 6,379,385 B1 | 4/2002 | Kalas et al. |
| 6,383,221 B1 | 5/2002 | Scarborough et al. |
| 6,391,030 B1 | 5/2002 | Wagner et al. |
| 6,391,058 B1 | 5/2002 | Kuslich et al. |
| 6,395,030 B1 | 5/2002 | Songer et al. |
| 6,395,031 B1 * | 5/2002 | Foley et al. ............... 623/17.11 |
| 6,395,032 B1 | 5/2002 | Gauchet |
| 6,395,034 B1 | 5/2002 | Suddaby |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoech et al. |
| 6,425,920 B1 | 7/2002 | Hamada |
| 6,432,106 B1 | 8/2002 | Fraser |
| 6,436,098 B1 | 8/2002 | Michelson |
| 6,436,119 B1 | 8/2002 | Erb et al. |
| 6,436,140 B1 | 8/2002 | Liu et al. |
| 6,436,142 B1 | 8/2002 | Paes et al. |
| 6,440,168 B1 | 8/2002 | Cauthen |
| 6,443,990 B1 | 9/2002 | Aebi et al. |
| 6,447,512 B1 | 9/2002 | Landry et al. |
| 6,447,544 B1 | 9/2002 | Michelson |
| 6,447,547 B1 | 9/2002 | Michelson |
| 6,451,019 B1 | 9/2002 | Zucherman et al. |
| 6,451,020 B1 | 9/2002 | Zucherman et al. |
| 6,454,804 B1 | 9/2002 | Ferree |
| 6,454,807 B1 | 9/2002 | Jackson |
| 6,458,131 B1 | 10/2002 | Ray |
| 6,458,159 B1 | 10/2002 | Thalgott |
| 6,461,359 B1 | 10/2002 | Tribus et al. |
| 6,468,310 B1 | 10/2002 | Ralph et al. |
| 6,471,724 B2 | 10/2002 | Zdeblick et al. |
| 6,475,219 B1 | 11/2002 | Shelokov |
| 6,478,796 B2 | 11/2002 | Zucherman et al. |
| 6,478,822 B1 | 11/2002 | Leroux et al. |
| 6,478,823 B1 | 11/2002 | Michelson |
| 6,482,233 B1 | 11/2002 | Aebi et al. |
| 6,482,235 B1 | 11/2002 | Lambrecht et al. |
| 6,485,517 B1 | 11/2002 | Michelson |
| 6,488,710 B2 | 12/2002 | Besselink |
| 6,500,178 B2 | 12/2002 | Zucherman et al. |
| 6,500,205 B1 | 12/2002 | Michelson |
| 6,503,279 B1 | 1/2003 | Webb et al. |
| 6,514,256 B2 | 2/2003 | Zucherman et al. |
| 6,517,580 B1 | 2/2003 | Ramadan et al. |
| 6,520,993 B2 | 2/2003 | James et al. |
| 6,520,996 B1 | 2/2003 | Manasas et al. |
| 6,524,312 B2 | 2/2003 | Landry et al. |
| 6,527,773 B1 | 3/2003 | Lin et al. |
| 6,527,804 B1 | 3/2003 | Gauchet et al. |
| 6,527,806 B2 | 3/2003 | Ralph et al. |
| 6,530,933 B1 | 3/2003 | Yeung et al. |
| 6,530,955 B2 | 3/2003 | Boyle et al. |
| 6,540,785 B1 | 4/2003 | Gill et al. |
| 6,547,823 B2 | 4/2003 | Scarborough et al. |
| 6,548,002 B2 | 4/2003 | Gresser et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec et al. |
| 6,565,570 B2 | 5/2003 | Sterett et al. |
| 6,569,201 B2 | 5/2003 | Moumene et al. |
| 6,572,653 B1 * | 6/2003 | Simonson ................. 623/17.13 |
| 6,572,654 B1 * | 6/2003 | Santilli ..................... 623/17.16 |
| 6,575,982 B1 | 6/2003 | Bonutti |
| 6,576,016 B1 | 6/2003 | Hochshuler et al. |
| 6,576,017 B2 | 6/2003 | Foley et al. |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,432 B1 | 6/2003 | Michelson |
| 6,582,437 B2 | 6/2003 | Dorchak et al. |
| 6,582,468 B1 | 6/2003 | Gauchet |
| 6,610,089 B1 * | 8/2003 | Liu et al. .................. 623/17.11 |
| 6,610,093 B1 * | 8/2003 | Pisharodi ................. 623/17.15 |
| 6,648,917 B2 * | 11/2003 | Gerbec et al. ............ 623/17.11 |
| 6,682,562 B2 | 1/2004 | Viart et al. |
| 6,706,068 B2 | 3/2004 | Ferree |
| 6,706,070 B1 | 3/2004 | Wagner et al. |
| 6,740,118 B2 | 5/2004 | Eisermann et al. |
| 6,755,841 B2 | 6/2004 | Fraser et al. |
| 6,770,095 B2 | 8/2004 | Grinberg et al. |
| 6,893,466 B2 | 5/2005 | Trieu |
| 7,128,760 B2 * | 10/2006 | Michelson ................ 623/17.15 |
| 7,204,853 B2 * | 4/2007 | Gordon et al. ........... 623/17.16 |
| 7,217,291 B2 * | 5/2007 | Zucherman et al. ...... 623/17.15 |
| 7,250,060 B2 * | 7/2007 | Trieu ....................... 623/17.15 |
| 7,255,714 B2 * | 8/2007 | Malek ...................... 623/17.15 |
| 7,331,995 B2 * | 2/2008 | Eisermann et al. ........ 623/17.14 |
| 7,351,261 B2 * | 4/2008 | Casey ...................... 623/17.13 |
| 2002/0128715 A1 | 9/2002 | Bryan et al. |
| 2002/0138146 A1 * | 9/2002 | Jackson ................... 623/17.15 |
| 2003/0149483 A1 * | 8/2003 | Michelson ............... 623/17.11 |
| 2003/0208273 A1 | 11/2003 | Eisermann et al. |
| 2004/0073313 A1 | 4/2004 | Link et al. |
| 2004/0106998 A1 | 6/2004 | Ferree |
| 2004/0117022 A1 | 6/2004 | Marnay et al. |
| 2004/0138750 A1 | 7/2004 | Mitchell |
| 2004/0143332 A1 | 7/2004 | Krueger |
| 2004/0225360 A1 | 11/2004 | Malone |
| 2004/0225365 A1 | 11/2004 | Eisermann et al. |
| 2004/0225366 A1 | 11/2004 | Eisermann et al. |
| 2004/0254644 A1 * | 12/2004 | Taylor ..................... 623/17.13 |
| 2005/0171609 A1 * | 8/2005 | Humphreys et al. ...... 623/17.15 |
| 2005/0171610 A1 * | 8/2005 | Humphreys et al. ...... 623/17.15 |
| 2006/0004454 A1 * | 1/2006 | Ferree et al. ............. 623/17.15 |
| 2006/0036326 A1 * | 2/2006 | Baumgartner et al. .... 623/17.15 |
| 2006/0069438 A1 * | 3/2006 | Zucherman et al. ...... 623/17.14 |
| 2007/0010887 A1 * | 1/2007 | Williams et al. .......... 623/17.15 |
| 2007/0083265 A1 * | 4/2007 | Malone .................... 623/17.11 |
| 2008/0015698 A1 * | 1/2008 | Marino et al. ............ 623/17.15 |
| 2008/0021557 A1 * | 1/2008 | Trieu ....................... 623/17.15 |
| 2008/0027549 A1 * | 1/2008 | Kirschman ............... 623/17.15 |
| 2008/0077242 A1 * | 3/2008 | Reo et al. ................. 623/17.15 |
| 2008/0114453 A1 * | 5/2008 | Francis .................... 623/17.14 |

FOREIGN PATENT DOCUMENTS

| | | |
|---|---|---|
| DE | 4012622 | 7/1991 |
| EP | 0307241 B1 | 3/1989 |
| FR | 2707864 | 1/1995 |
| FR | 2717066 | 9/1995 |
| FR | 2717068 | 9/1995 |
| FR | 2730156 A1 | 9/1996 |
| FR | 2780269 A1 | 12/1999 |
| FR | 2806614 A1 | 9/2001 |
| WO | WO 90/00037 | 1/1990 |
| WO | WO 95/31158 A | 11/1995 |
| WO | WO 99/26562 | 6/1999 |
| WO | WO 99/59669 | 11/1999 |

| | | |
|---|---|---|
| WO | WO 00/04851 | 2/2000 |
| WO | WO 00/13619 | 3/2000 |
| WO | WO 00/13620 | 3/2000 |
| WO | WO 00/23015 A1 | 4/2000 |
| WO | WO 01/01893 A1 | 1/2001 |
| WO | WO 01/89428 A2 | 11/2001 |

OTHER PUBLICATIONS

Waldemar Link brochure entitled "Wirbelsäulen-Chirurgie: Instrumentarium Und Implantate Zur Wirbelsäulen-Chirurgie (Spinal Surgery: Instrumentation and Implants for Spinal Surgery)", Waldermar Link, Hamburg, Germany (1971).

Porter, Richard W., "Spinal Stenosis and Neurogenic Claudication", Spine vol. 21, No. 17, pp. 2046-2052, Lippincott-Raven Publishers (1996).

Minns, R.J. et al., "Preliminary Design and Experimental Studies of a Novel Soft Implant for Correcting Sagittal Plan Instability in the Lumbar Spine", Spine vol. 22, No. 16, pp. 1819-1827, Lippincott-Raven Publishers (1997).

* cited by examiner

MULTI-PIECE ARTIFICIAL SPINAL DISK REPLACEMENT DEVICE WITH SELECTABLY POSITIONING ARTICULATING ELEMENT

PRIORITY CLAIM

This application claims priority to the following three provisional applications, which are each hereby incorporated by reference in their entirety:

MULTI-PIECE ARTIFICIAL SPINAL DISK REPLACEMENT DEVICE WITH SELECTABLY POSITIONING ARTICULATING ELEMENT, U.S. Provisional Patent Application No. 60/614,246, filed on Sep. 29, 2004, Inventors: James Zucherman and Ken Y. Hsu;

MULTI-PIECE ARTIFICIAL SPINAL DISK REPLACEMENT DEVICE WITH MULTI-SEGMENTED SUPPORT PLATES, U.S. Provisional Patent Application No. 60/614,061, filed on Sep. 29, 2004, Inventors: James Zucherman and Ken Y. Hsu;

POSTERIOR APPROACH IMPLANT METHOD FOR ASSEMBLY OF A MULTI-PIECE ARTIFICIAL SPINAL DISK REPLACEMENT DEVICE IN SITU, U.S. Provisional Patent Application No. 60/614,181, filed on Sep. 29, 2004, Inventors: James Zucherman and Ken Y. Hsu.

CROSS REFERENCES TO RELATED APPLICATIONS

This application is related to the following co-pending applications which are each hereby incorporated by reference in their entirety:

POSTERIOR APPROACH IMPLANT METHOD FOR ASSEMBLY OF A MULTI-PIECE ARTIFICIAL SPINAL DISK REPLACEMENT DEVICE IN SITU, U.S. patent application Ser. No. 10/979,841, filed on Nov. 2, 2004, Inventors: James Zucherman and Ken Y. Hsu.

MULTI-PIECE ARTIFICIAL SPINAL DISK REPLACEMENT DEVICE WITH MULTI-SEGMENTED SUPPORT PLATES, U.S. patent application Ser. No. 10/979,850, filed on Nov. 2, 2004, Inventors: James Zucherman and Ken Y. Hsu.

FIELD OF THE INVENTION

This invention relates to multi-piece artificial vertebral disk replacement implants with a selectably positionable articulating element and techniques for assembling the implant in situ via a posterior approach.

BACKGROUND OF THE INVENTION

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and nerve roots.

As the present society ages, it is anticipated that there will be an increase in adverse spinal conditions which are characteristic of older people. Pain associated with such conditions can be relieved by medication and/or surgery. Of course, it is desirable to eliminate the need for major surgery for all individuals and in particular for the elderly.

More particularly, over the years, a variety of intervertebral implants have been developed in an effort to relieve the pain associated with degenerative and dysfunctional disk conditions. For example, U.S. Pat. No. 4,349,921 to Kuntz discloses an intervertebral disk prosthesis that consists of two prosthesis parts that are positioned side-by-side between adjacent vertebrae. The two parts together are said to replace the function of a natural intervertebral disk. This patent also discloses that the two parts can be implanted by a posterior approach.

U.S. Pat. No. 4,714,469 to Kenna discloses a spinal implant that fuses vertebrae to the implant. The implant has a rigid body that fits between the vertebrae with a protuberance extending from a vertebral contacting surface and extends into the vertebral body.

U.S. Pat. Nos. 4,772,287 and 4,904,260 both to Ray et al. disclose implanting two prosthetic disc capsules side-by-side into the nucleus of the annulus of a damaged disk. The capsules are filled with a fluid.

U.S. Pat. No. 5,562,736 to Ray et al. discloses a surgical procedure for implanting a prosthetic spinal disk nucleus into a spinal disk space through a posterior side of the annulus.

U.S. Pat. No. 5,258,031 to Salib et al. discloses another prosthetic disk with a ball that fits into a socket.

U.S. Pat. Nos. 5,425,773 and 5,562,738 both to Boyd et al. disclose a disk arthroplasty device for replacement of the spinal disk. A ball-and-socket are provided to enable rotation.

U.S. Pat. No. 5,534,029 to Shima discloses an articulated vertebral body spacer with a pair of upper and lower joint pieces inserted between the vertebrae. An intermediate layer is provided to allow for movement between the upper joint piece and the lower joint piece.

U.S. Pat. No. 5,782,832 to Larsen et al. discloses a two-piece ball-and-socket spinal implant with upper and lower plates for insertion within the intervertebral space.

U.S. Pat. No. 6,156,067 to Bryan et al. discloses a prosthesis having two plates with a nucleus there between.

Prior art implants do not include mechanisms that permit the surgeon the adjust the position where the weight bearing and rotating surface of the device to be located. Finally, the posterior approach surgical procedures disclosed are limited to implanting relative small devices.

Even given the above devices, the art is in search of enhanced implants for alleviating adverse spinal conditions and for restoring natural movement to the spinal column wherein the implant has an articulating element with an articulating surface that can be positioned in one of multiple positions within the device. In addition, the art is in need of surgical techniques for implanting large devices and especially multiple-piece devices between vertebrae by a posterior approach.

DETAILED DESCRIPTION OF THE PREFERRED EMBODIMENTS OF THE INVENTION

Figure 1A:
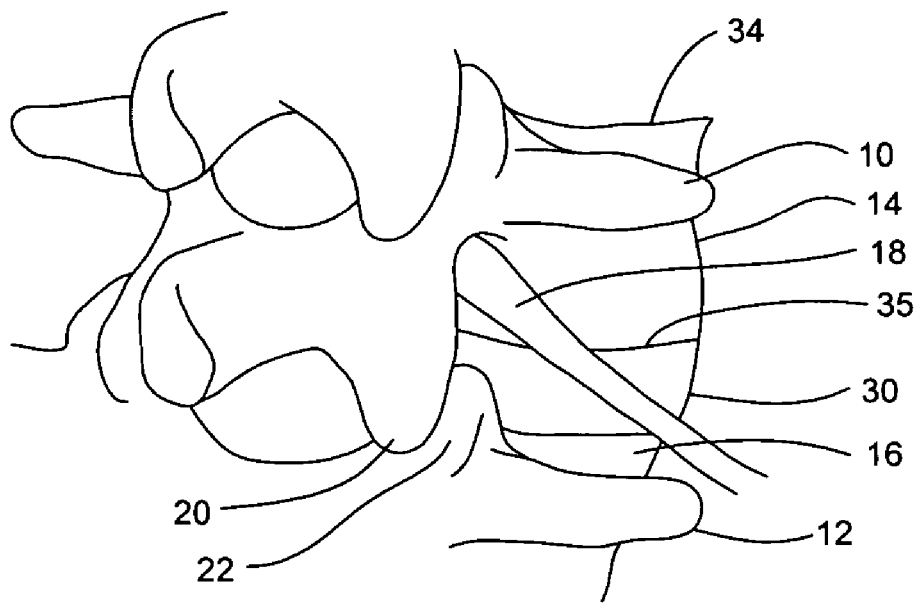
FIG. 1A is a posterior elevational partial view of the spinal column.

Embodiments of the present invention are directed to an intervertebral implant for alleviating discomfort associated with the spinal column. The implant is characterized by having a first end plate, a second end plate, and an articulating element that is situated between them. The articulating element can be located in one of a plurality of selectable, positions between the first and second end plates. The articulating element functions as a weight bearing member and includes a curved or convex exterior articulating surface that rests within a recess that serves as a support surface of the first end plate. The articulating element enables the end plates to move relative to each other.

A posterior approach for intervertebral disk replacement is also provided. This technique is particularly suited for assembling a multi-piece artificial spinal disk replacement device in situ in order to alleviate discomfort associated with the spinal column.

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Other aspects, objects, features and elements of embodiments of the invention are directed or evident from the accompanying claims and figures.

In one embodiment, the invention provides a technique for implanting a "large" artificial spinal replacement device or implant via a posterior approach to the spine. The term "large" is meant that the width of the device (or individual pieces that form the device) implanted is longer than both the width and height of a substantially rectangular-shaped opening that is created through the annulus by a posterior annulotomy and through which the device (or individual pieces thereof) is positioned into the nucleus pulposis (or the intervertebral space created by its removal).

The inventive procedure is particularly suited for assembling in situ a multi-piece artificial spinal disk replacement device wherein at least one of the pieces of the device preferably has a width that is longer than both the width and height of the substantially rectangular-shape opening in the annulus. Accordingly, the individual pieces of the devices are inserted through this opening and the pieces are assembled within the nucleus pulposis (or the intervertebral space created by its removal) to form the multi-piece device. By "multi-piece" device is meant a spinal disk replacement device having at least two parts or pieces that cooperate with each other in distributing weight through the spine and similulating motion of the spine. Preferred multi-piece devices when assembled have pieces that are positioned one on top of the other along a vertical axis.

Figure 1B:
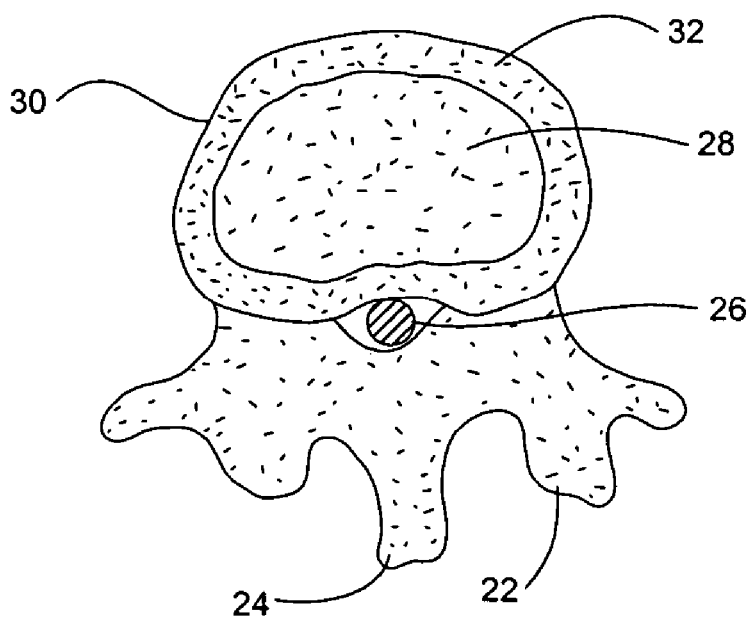
FIG. 1B is a transaxial view of the spine.

Referring to FIGS. 1A and 1B, the spinal column includes successive vertebrae 10 and 12 with vertebral bodies 14 and 16, respectively. A vertebral disk 30, which is situated between the vertebral bodies 14, 16, includes an outer annulus fibrosis 32 and an inner nucleus pulposis 28. The annulus fibrosis 32 is a ligamentous ring which binds the adjacent vertebrae 10, 12 together. The body 14 of the vertebra 10 has concave upper and lower surfaces 34, 35 respectively with raised marginal edges. A layer of cartilage covers the body surfaces 34, 35. The neural canal contains the cauda equina or spinal cord 26. Various processes 24 extend from the body and these shield the spinal cord 26 and provide attachment sites for muscles. Nerves 18 extend from the spinal cord 26 in the interstices of the processes. The annulus fibrosis 32 along with the facet joints 20, 22 restrict the torsional motion or twisting between vertebrae.

Figure 2A:
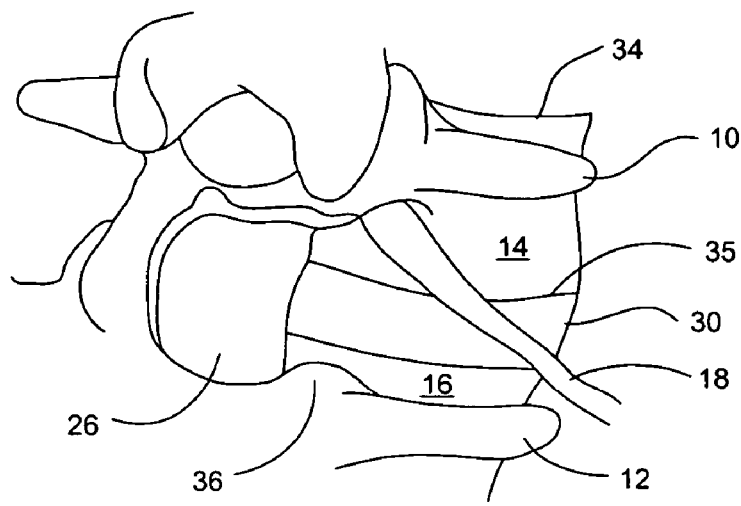
FIG. 2A is a posterior elevational partial view of the spinal column showing the unilateral facet removal.
Figure 2B:
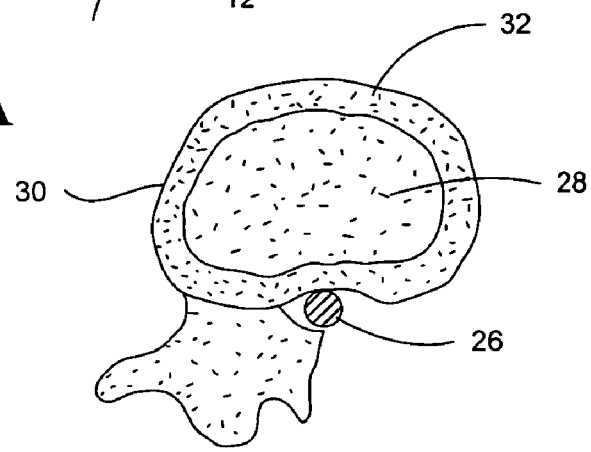
FIG. 2B shows a transaxial view of the spine after the unilateral facet removal.

The steps for replacing the nucleus pulposis of the disk through a posterior approach with an artificial spinal disk replacement device are shown in FIGS. 2A through 2C, and FIGS. 3A through 3F. FIGS. 2A and 2B show the exposed affected region of the spine posteriorly after unilateral facet removal from vertebrae 10 and 12. Pedicle 36 of vertebra 12 may be left in.

Figure 2C:
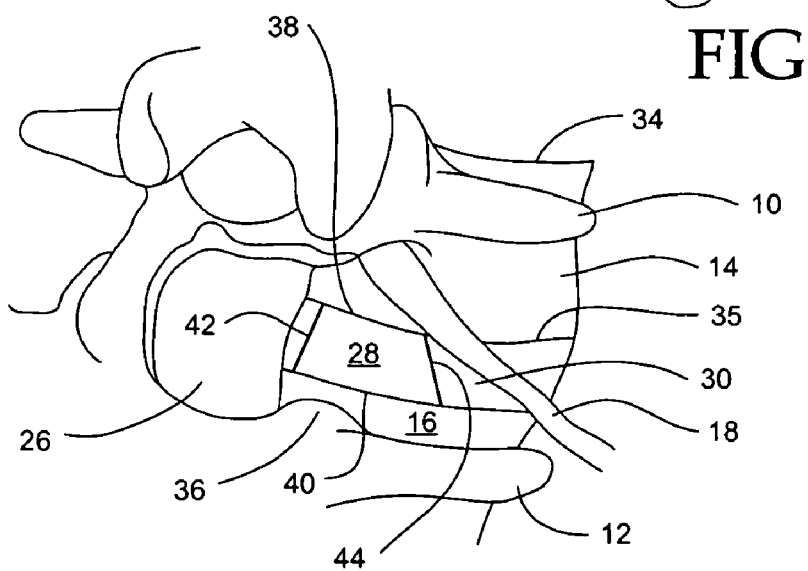
FIG. 2C is a posterior elevational partial view of the spinal column showing the removal of a portion of the annulus.

Following the unilateral facet removal, as shown in FIG. 2C, the surgeon performs an annulotomy whereby a flap (not shown) is cut from the posterior annulus 32 to expose the nucleus pulposis 28. As is apparent, the opening is substantially rectangular with upper and lower sides 38 and 40, and lateral sides 42 and 44. The upper side 38 is preferably substantially flushed with the lower surface of vertebral body 14 and the lower side 40 is preferably substantially flushed with the upper surface of vertebral body 16. The upper and lower surfaces of the vertebral bodies are also referred to as end plates. During the procedure, the caudal equina 26 can be moved by the surgeon to one side by a nerve root retractor. As shown, the inner side 42 of the opening is preferably near the midsiggital plane of the disk 30. Next, a portion of the nucleus pulposus corresponding to the space that will be occupied by the assembled multi-piece is removed.

Figure 3A:
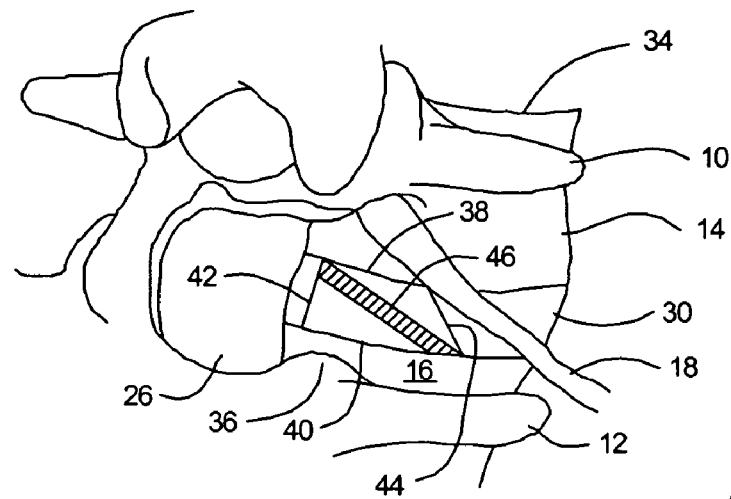
FIG. 3A is the posterior elevational partial view of the spinal column showing the initial insertion of an implant through a posterior annulotomy.
Figure 3B:
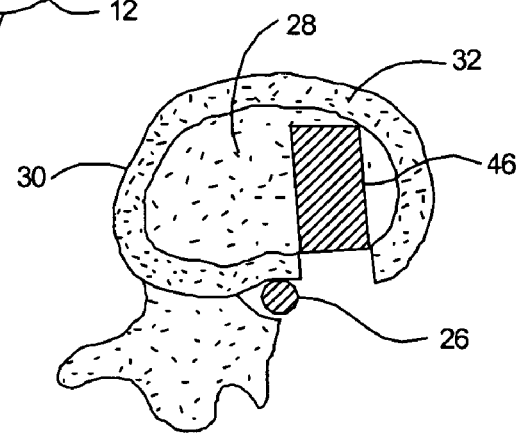
FIG. 3B is the transaxial view of the spine showing the initial insertion of the implant.
Figure 3C:
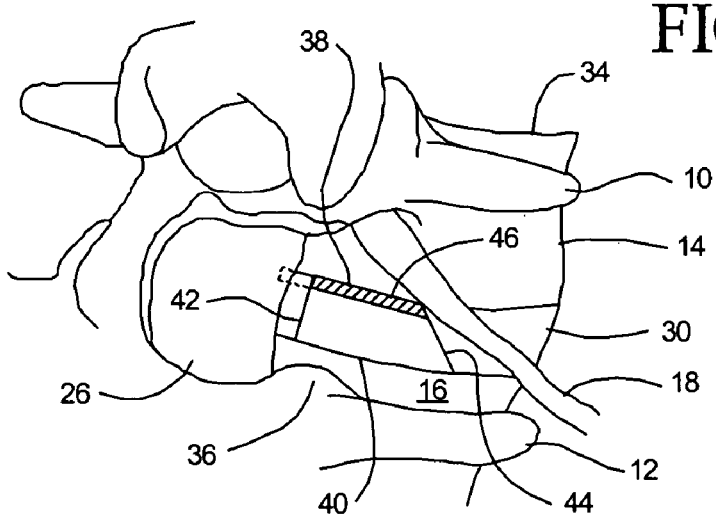
FIG. 3C is the posterior elevational partial view of the spinal column showing the positioning of the implant against the end plate or lower surface of the upper vertebra.
Figure 3D:
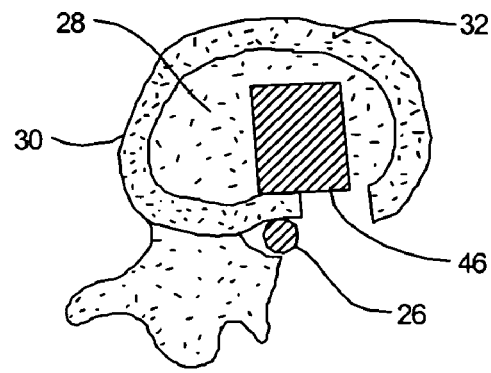
FIG. 3D is the transaxial view of the spine showing the positioning of the implant against the upper vertebra.

In the case where the device to be implanted does not include any piece (or pieces) that has a particularly long width vis-à-vis the dimensions of the disk being treated or replaced, the dimensions of the opening created by the annulotomy can be such that the diagonal of the opening will accommodate the a device as shown in FIG. 3A. The first piece 46 of the multi-piece device is inserted through the opening of the posterior annulus with the with of the first piece being positioned along the diagonal of the opening. The first piece 46 is inserted into the disk in the posterior-to-anterior direction as shown in FIG. 3B. Thereafter, as shown in FIGS. 3C and 3D, the first piece 46 is maneuvered so that its upper surface is parallel to and in contact with the lower surface of the upper vertebra. An implantation tool can be used to hold the first piece 46 in place. The implantation tool can include one or more prongs that are received in the bores of the first piece 46 in order to hold the first piece 46 in place. It is preferred that at least part of the first piece 46 be urged laterally and be aligned so as to occupy space at the midsiggital region of the disk as shown in FIG. 3D. This can be achieved by moving the first piece 46 toward the center region of the disk. As will be apparent, this allows the multi-piece device, once assembled, to better support the weight that is placed upon it and to simulate the natural movement of the spine.

Figure 3E:
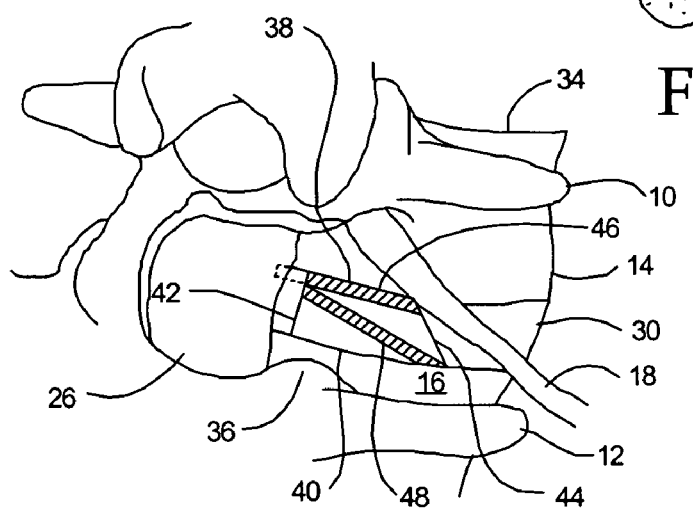
FIG. 3E is the posterior elevational partial view of the spinal column showing the initial insertion of a second implant through the posterior annulotomy.
Figure 3F:
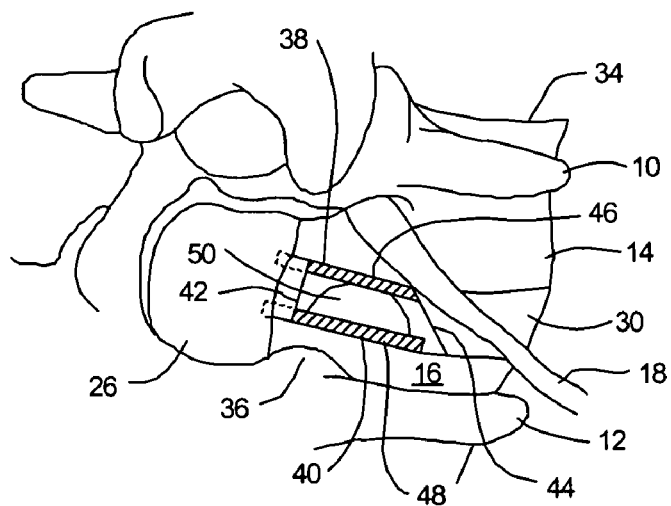
FIG. 3F is the posterior elevational partial view of the spinal column showing the insertion of a third implant through the posterior annulotomy wherein the third implant is positioned between the first and second implants.

Using the same procedure, the second piece 48 of the multi-piece device is inserted through the opening as shown in FIG. 3E with the width of the second piece 48 being positioned along the diagonal of the remaining portion of the opening. Thereafter, the second piece 48 is maneuvered, using a tool similar to the first piece 46, so that its lower surface is parallel to and in contact with the upper surface of the lower vertebra 16. Finally, a third piece 50 of the multi-piece device is inserted between the first and second pieces as shown in FIG. 3F. As will be further described herein, the third piece 50 includes an articulating surface which allows the first and second pieces to move relative to each other.

With the inventive procedure, it is preferred that the pieces of a multi-piece device be inserted through the opening at the annulus in sequence according to size, i.e., width, with the piece with the largest width being inserted first. In this fashion, the multi-piece device can be readily assembled in situ, that is, within the disk region affected.

Figure 4:
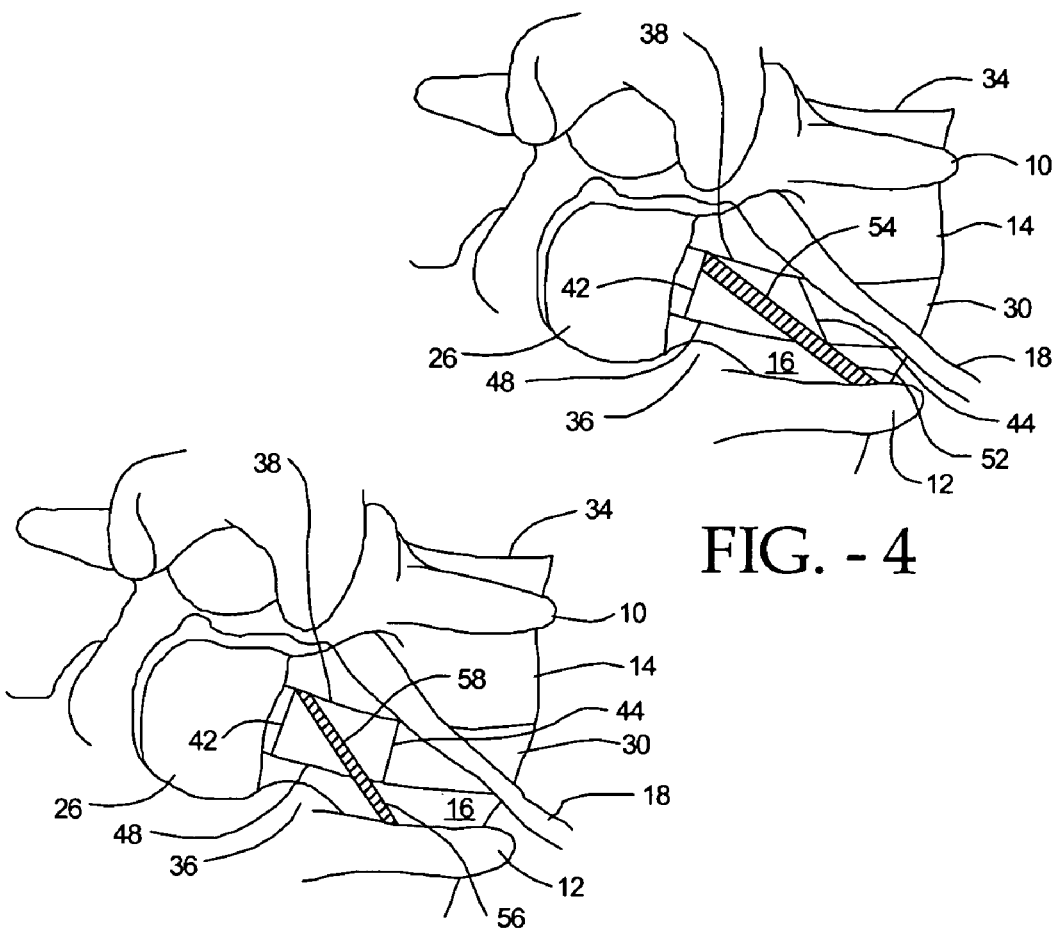
FIGS. 4, 5, and 6 are the posterior elevational partial views of the spinal column showing the initial insertions of three different sized implants through a posterior annulotomy.

In cases where the device to be implanted does include a piece (or pieces) that has a particularly long width vis-à-vis the dimensions of the disk being treated or replaced, it may be necessary to remove bone from the vertebral body and/or process of the vertebra to accommodate the larger dimensions. As shown in FIG. 4, bone is removed, e.g., drilled, to create a slot 52 in the vertebral body 16. The combined length of the slot 52 and the diagonal of the opening is approximately equal to the width of the piece 54. As is apparent, the slot 52 and the diagonal are co-axial. The piece 54 is initially inserted through the slot 52 and the opening; thereafter, the piece 54 is urged laterally and aligned into the position as described previously (FIG. 3D).

Figure 5:
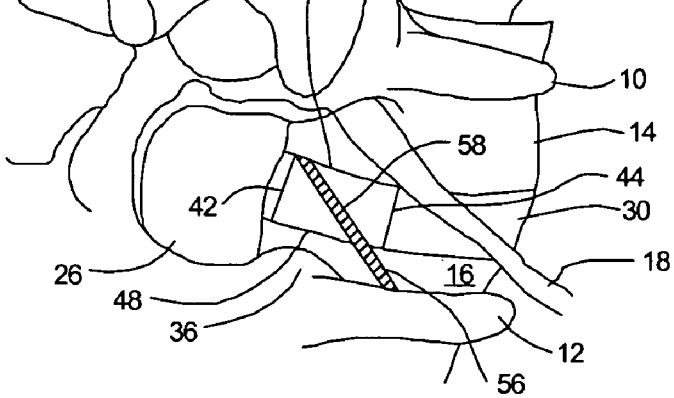

Similarly, as shown FIG. 5, bone is removed to create a slot 56 in the vertebral body 16. In this case, the slot 56 and the diagonal are not co-axial, rather, the slot 56 is drilled away from the corner of the rectangular opening. This procedure may be necessary in case of anatomical constraints. Piece 58 is initially inserted through the slot 56 and the opening. Thereafter, the piece 58 is urged laterally and aligned into the position as described previously.

Figure 6:
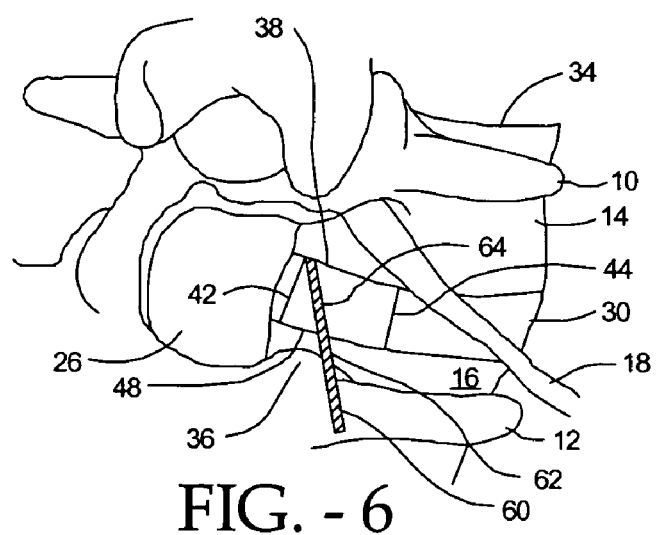

Finally, FIG. 6 shows an embodiment where a slot 60 is made in the pedicle 36 and a second slot 62 is made in the vertebral body 16. Piece 64 is initially inserted through the slots 60, 62 and the opening. Thereafter, the piece 64 is urged laterally and aligned into the position as described previously. The above slots 52, 56 and 62 are each also suitable for inserting a keel or similar apparatus into the vertebra body support and anchor the piece 64 or any other part of the device as will be described below.

Figure 7A:
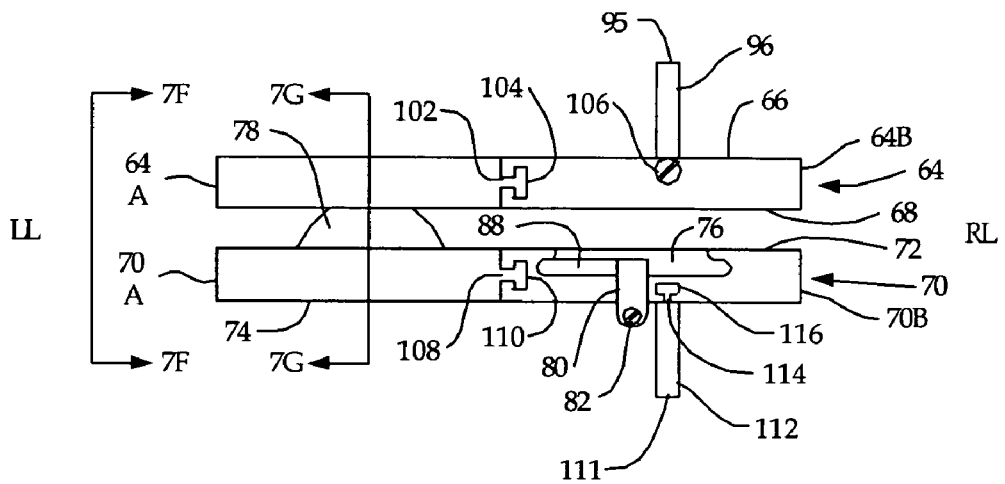
FIG. 7A is a posterior elevational partial view of an assembled multi-piece implant in its neutral position having a first or upper end plate, a second or lower end plate, and an articulating element between the first and second end plates.
Figure 7B:
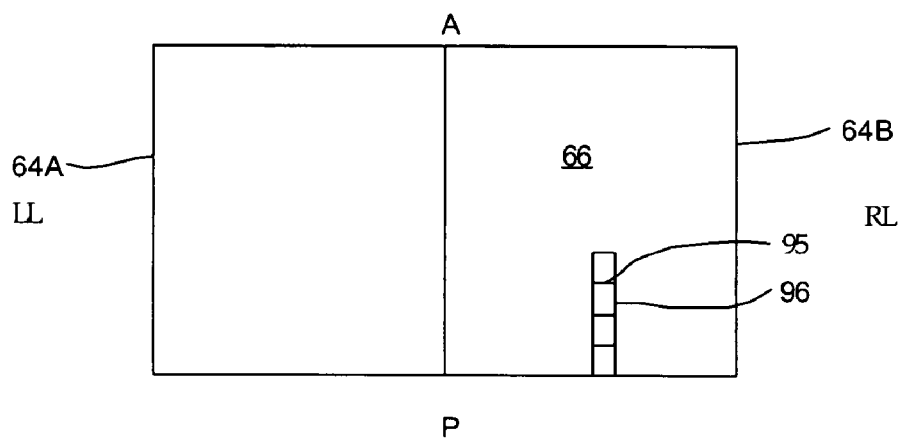
FIG. 7B is the plan view of the outer surface of the first end plate of the implant.

FIGS. 7A through 7H illustrate a multi-piece device that can be assembled in situ with the above described posterior techniques. The device has a selectably positionable articulating element. The designations, "A" for anterior, "P" for posterior, "RL" for right lateral, and "LL" for left lateral are given in the drawings for spatial orientation. These designations give the relationship of all faces of implant from the superior perspective; i.e., looking down the axis of the spine. (The device in FIG. 7A is shown in its neutral position where the first and second end plates have not moved relative to each other.) The assembled implant includes (i) a first end plate 64, which is formed from first and second upper end plate segments 64A and 64B, wherein the first end plate 64 is configured to mate with a first vertebra and (ii) a second end plate 70, which is formed from first and second lower end plate segments 70A and 70B, wherein the second end plate 70 is configured to mate with a second vertebra.

As shown in FIG. 7A, the first and second upper segments 64A and 64B are fixedly connected by a tongue 102 and groove 104 arrangement at the sides of the two segments to form a rigid horizontal plate having an outer surface 66 that can be positioned against a first vertebra body when the implant is implanted. The first end plate 64 can be secured to the upper vertebral body with a keel 96 that has a tongue (see tongue 114 of keel 112) at its proximal end. The tongue fits snugly within a groove that is formed on the outer surface 66. To prevent dislodgement of the keel 96, a screw 106 is screwed into the posterior side of the first end plate 64 to secure the tongue in position. The keel 96 can have teeth 95 on its upper surface. For a posterior approach, the teeth 95 of the keel 96 would be pointed toward the posterior in order to aid in retaining the implant in place.

Similarly, the first and second lower segments 70A and 70B are fixedly connected by a tongue 108 and groove 110 arrangement at the sides of the two segments to form a rigid horizontal plate having an outer surface 74 that can be positioned against a second vertebra body when the implant is implanted. The second end plate 70 can be secured to the lower vertebral body with a keel 112 that has a tongue 114 at its proximal end. The tongue fits snugly within a groove 116 that is formed on the first surface 74 as shown in FIG. 7A. If desired, a screw can also be screwed into the posterior side of the second end plate 70 to secure the tongue 114 in position. The keel 112 can have teeth 111 on its upper surface. For a posterior approach, the teeth 111 of the keel 112 would be pointed toward the posterior in order to aid in retaining the implant in place.

Figure 7C:
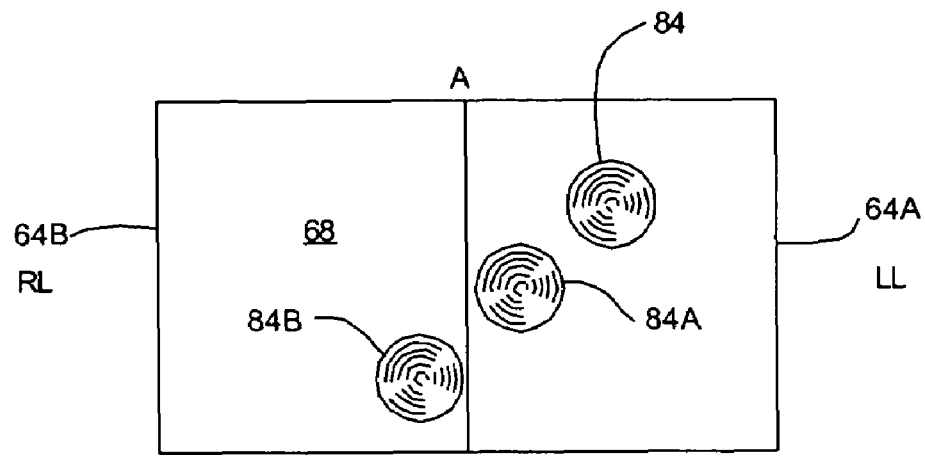
FIG. 7C is the plan view of the inner surface of the first end plate of the implant.

As shown in FIG. 7C, the second or inner surface 68 of the first end plate 64 defines three recesses 84, 84A and 84B that are arranged linearly in this embodiment. Each recess has a curved or concave surface that can support an articulating element. Although three recesses are shown, it is understood that the inner surface 68 can include multiple recesses with the number of linearly arranged recesses preferably ranging from 2 to 4. As further explained herein, the presence of these multiple recesses allows the surgeon to select the best location where the articulating element is to be placed. The dimensions of the three recesses can be the same or different. While each recess will have a contour matching that of the upper exterior articulating surface of the articulating element, the depth of each recess can differ. A recess that is deeper will be in contact with a greater area of the articulating surface, but the greater depth means that the first end plate 64 will be closer to the second end plate 70 when the implant is in its neutral position.

Figure 7D:
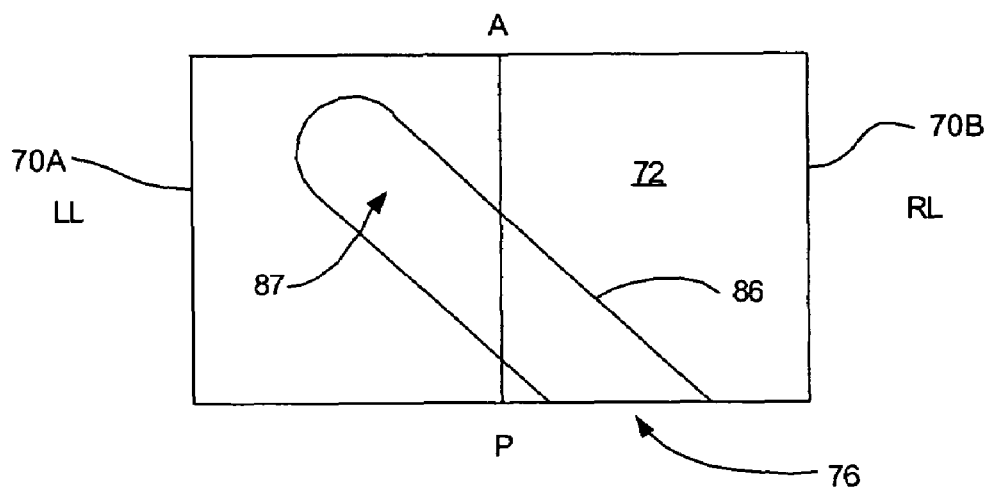
FIG. 7D is the plan view of the inner surface of the second end plate of the implant.
Figure 7E:
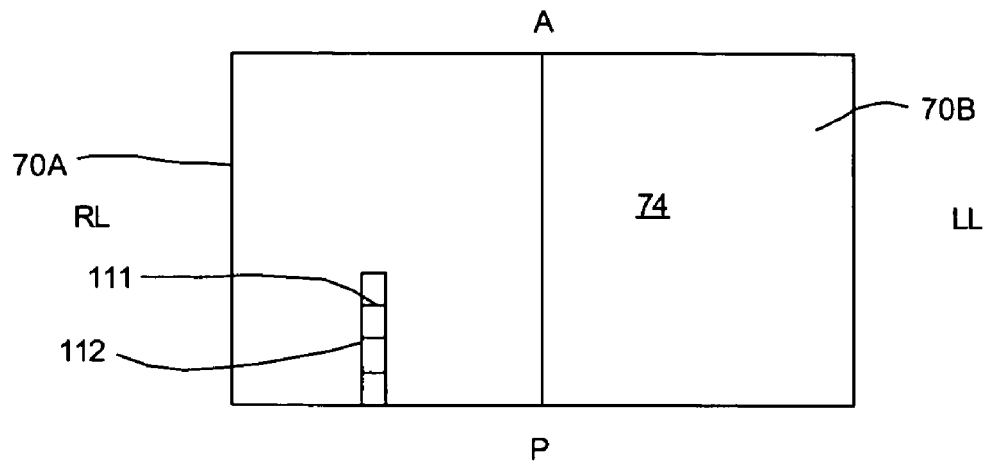
FIG. 7E is the plan view of the outer surface of the second end plate of the implant.

As shown in FIG. 7D, the second end plate 70 has a groove 86 that is formed on its inner surface 72. The groove 86 has an entrance 76 on the posterior surface of the second end plate 70 which defines a guide channel 87 that traverses the approximate length of the second end plate 70 from the posterior surface toward the anterior surface of the second end plate 70. The axis through the center of the groove 86 is slanted relative to the sagital plane of the implant so that while the entrance 76 is located at the posterior surface of the first lower segment 70B, the groove is directed toward the center and terminate at the second lower segment 70A. When the first and second end plates 64, 70 are assembled, the groove 86 is aligned with and faces the linear arrangement of the three recesses 84, 84A and 84B as shown in FIG. 7C.

While each of the first and second end plates 68, 70 is illustrated as being fabricated of two segments, it is understood that either plate can comprise more than two segments joined side by side, if desired. The number of segments needed will depend on, among other things, the dimensions of the intervertebral disk to be replaced and the dimensions of the opening in the posterior annulus available for insertion of the individual pieces. Furthermore, the numbers of segments forming the first end plate 64 can be different from that forming the second end plate 70. Regardless of the number of segments employed, it is preferred that the overall length and width of the first end plate 64 be substantially the same as that of the second end plate 70.

Figure 7F:
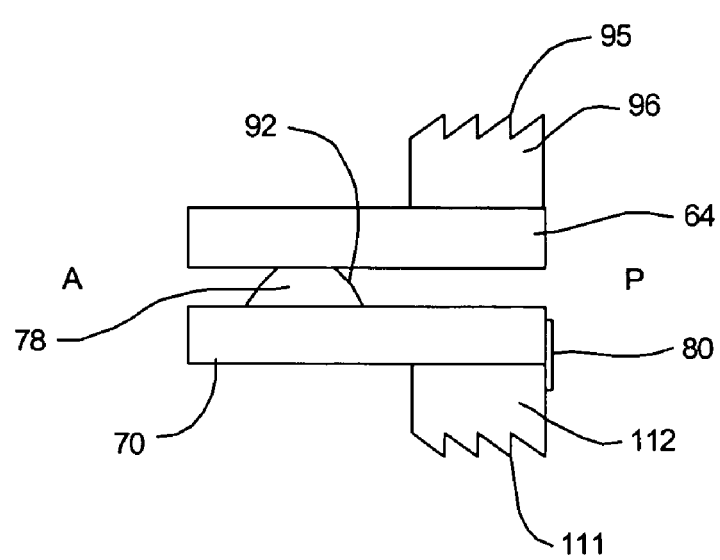
FIG. 7F is the side view of the implants along the 7F-7F line of FIG. 7A.
Figure 7G:
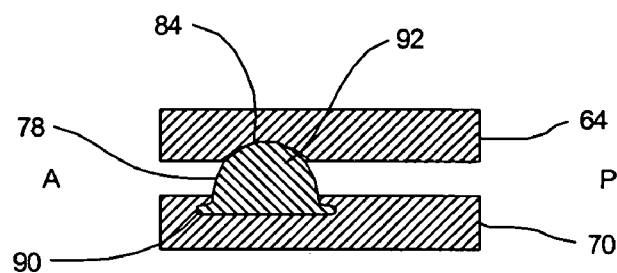
FIG. 7G is the cross-sectional view of along the 7G-7G line of FIG. 7A.
Figure 7H:
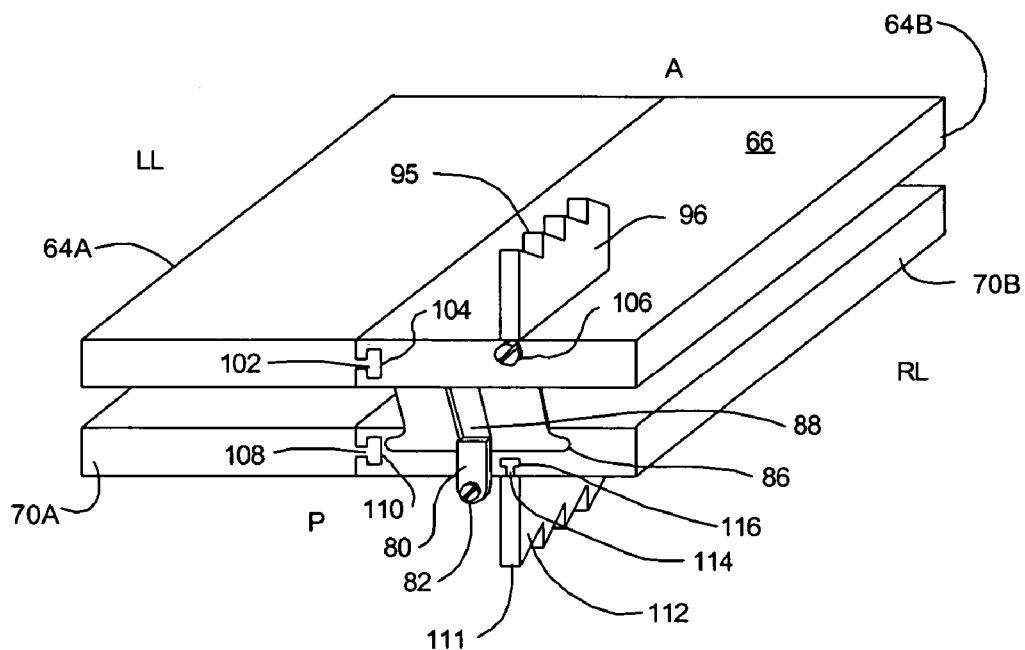
FIG. 7H is a perspective view of the assembled multi-piece implant.
Figure 8A:
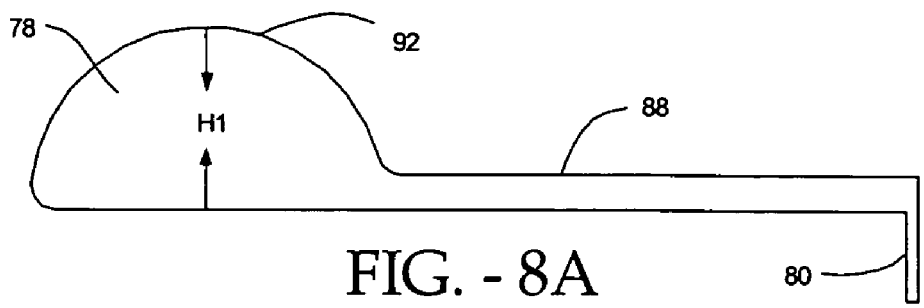
FIGS. 8A, 8B and 8C are the cross-sectional views of three third piece embodiments of the implant with each having an articulating surface.
Figure 8B:
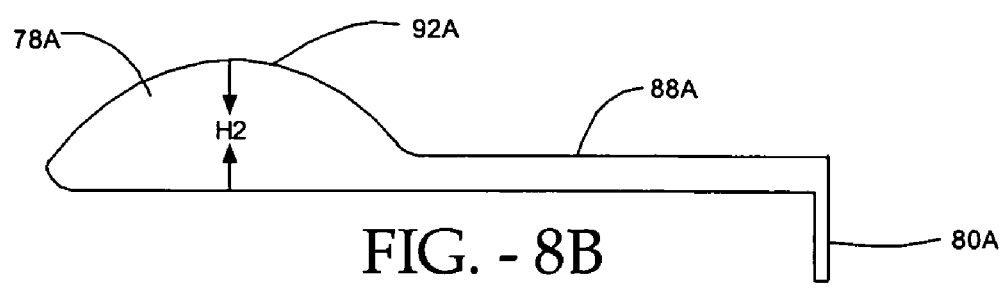
Figure 8C:
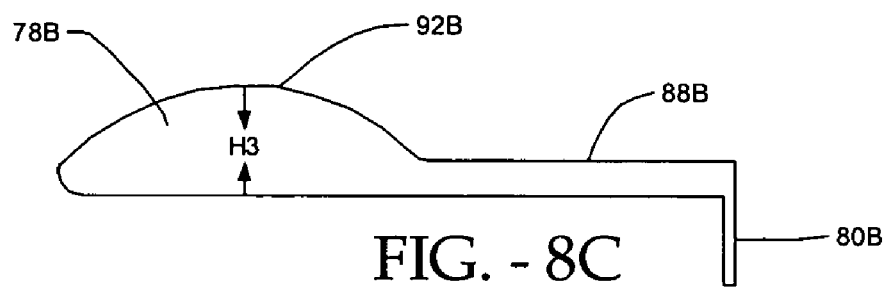
Figure 8D:
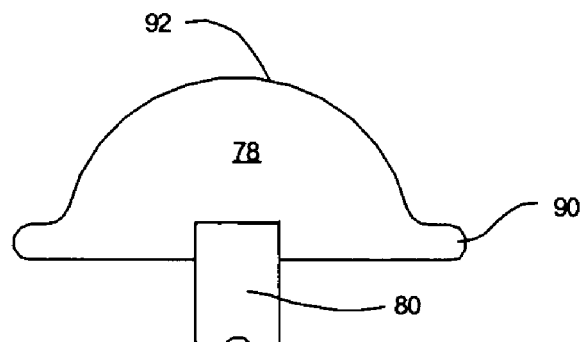
FIG. 8D is the back view of a third piece of the implant.

As shown in FIGS. 7A, 7F, and 7G, the assembled multi-piece implant includes a third piece 78 that is positioned between the first and second end plates 64, 70. The third piece has a circular beveled-shaped base 90 that fits within the groove 86 of the second end plate 70, and an upper articulating element 92 that has a convex exterior surface that substantially matches the contour of the exterior surface of the recess 84. In the embodiment illustrated, the third piece 78 has been positioned into recess 84 and not into either recess 84A or 84B. The articulating element 92, which comes into slidable contact with the recess 84, allows the first end plate 64 and second end plate 70 to pivot and/or rotate relative to each other. The third piece 78 includes a neck 88 and a strap or lip 80 at the distal end. The length of the neck 88 is designed so that once the third piece 78 is properly positioned between the first and second end plates 64, 70, the strap 80 contacts the posterior surface of second end plate 70. The third piece 78 is secured to the lower vertebral body with a screw 82 which passes through an opening on the strap 80.

The complementary configurations of the recess 84 and the exterior surface of the articulating element 92 allow the implant to simulate the natural motion of the spine. In a preferred embodiment, the articulating element 92 has a raised surface that is configured as a hemisphere and the corresponding recess 84 has a matching exterior contour shaped as a symmetrical circular cavity or concave cavity. The recess 84 covers only a portion of the surface area of the articulating element 92 at any given time. In this fashion, as the recess 84 traverses over different areas of the articulating element 92, the first end plate 64, in turn, moves relative to the second end plate 70. It is expected that the implant will restore natural movement to the patient thereby providing the patient with twisting or torsional movement as well as forward and backward bending motion, i.e., flexion and extension.

The dimensions of recesses 84A and 84B can be the same as those of recess 84. Alternatively, the dimensions of any two of the three recesses can be the same or the dimensions all three recesses can be different. Generally, the exterior contours of the three recesses will match the exterior contour of the articulating element 92, however the heights of the recesses can be different, if desired.

The level of movement can be tailored by appropriate design of the third piece of the multi-piece implant, although it is understood the intervertebral implant functions in conjunction with the unaffected (or natural) structures of the spinal column. For example, the inter-plate distance between the first and second end plates 64 and 70, that is, the distance between inner surface 68 of the first end plate 64 and the inner surface 72 of the second end plate 70, determines the degree of forward and backward bending. The greater the inter-plate distance, the higher degree of movement possible, subject to other conditions. This inter-plate distance depends on the depth of the recess on which the articulating element 92 rests and/or the height of the corresponding articulating element 92. Finally, the degree of movement of the first and second end plates 64 and 70 depends on which of the three recesses the articulating element 92 is positioned. In the case where the dimensions of all three recesses 84, 84A, and 84B are the same, then locating the articulating element 92 in recess 84 which is closest to the anterior surface (A) will afford the highest level of forward bending or flexion. Conversely, locating the articulating element 92 in recess 84B which is closest to the posterior surface (P) will afford the highest level of backward bending or extension. Finally, locating the articulating element 92 in recess 84A which is in the middle of the three recesses may afford a more balanced level of flexsion and extension.

The twisting action would generally be about an axis that is perpendicular to the first and second inner surfaces 68, 72 of the first and second end plates 64, 70, respectively. Thus, the implant of this embodiment allows the spine to have movement in three orthogonal degrees of freedom, namely (1) forward and backward bending movement, (2) lateral side-to-side bending, and (3) twisting movement.

In assembling the multi-piece implant illustrated in FIGS. 7A through 7H in situ, the spine is exposed and the first and second end plates 64, 70 are then positioned between adjacent vertebrae by a posterior approach as described previously. Thereafter, the surgeon selects the third piece of the appropriate length for insertion between the first and second end plates 64, 70 and into recess 84, 84A, or 84B. Because the entrance 76 of the groove 86 is to one side of the posterior surface of the second end plate 70, the surgeon can readily maneuver the third piece 78 through the entrance 76 and into the groove 86.

Referring to FIGS. 8A, 8B, 8C, and 8D the surgeon has three third pieces 78, 78A, and 78B from which to choose depending on which recess is used. The three pieces 78, 78A, and 78B have different length necks 88, 88A, and 88B, respectively, and, in these embodiments, articulating elements 78, 78A, and 78B have different heights (H). (The heights can be the same.) Each third piece includes a strap or lip 80, 80A, or 80B located its distal end. Alternatively, the three pieces can have the same dimensions, e.g. heights, except for their lengths. In practice, an array of third pieces having different articulating elements heights and/or and neck lengths will be available to the surgeon who has the option of evaluating each and selecting the most appropriate one. Regardless, of the third piece selected, when the third piece is in positioned in the neutral position, the center of the recess (i.e., 84, 84A or 84B) of the first end plate 64 rests substantially on the center of the articulating element.

Since the first end plate 64 consists of two segments joined side-by-side as shown in FIG. 7A, a preferred method of assembly the first end plate 64 is to first insert the first upper segment 64A through an opening in the posterior annulus and then maneuver it toward the middle of the intervertebral space. The first upper segment 64A is positioned such that its side tongue 102 is exposed. Next, the groove 104 of the second upper segment 64B is guided along the tongue 102 thereby connecting the two segments and, at the same time, inserting the second upper segment 64B into the intervertebral space. The assembled first end plate 64 is then positioned against the lower surface of the upper vertebral body. The second end plate 70 can be assembled within the intervertebral space by the same procedure of inserting the first lower segment 70A and followed by the second lower segment 70B.

Accordingly, the method of implantation is similar to that for the embodiments shown in FIGS. 3A-3F. That is to say that the same amount or less of bone is removed as shown in FIG. 3D. Then the first segment 64A of the first end plate is inserted and urged laterally in order to allow the second segment 64B to be inserted so that the first and second segments 64A and 64B can be assembled with the tongue and groove arrangement. The same procedure is used to insert and assemble in place the second end plate 70. With the end plates 64 and 70 in place, the articulation element 78 can be inserted through the same opening in the posterior annulus that the first and second end plates 64 and 70 are inserted. The articulation can then be urged in the groove of the second end plate 70 to the desired location. As is evident, the present embodiment has the advantage that the implant can be inserted and assembled through a posterior approach from any one side of the spinal canal. That is to say that access is not required from both posterior and lateral sides relative to the spinal column.

As shown in FIG. 7A, the keels 96 and 112 are typically perpendicular to the upper surface 66 and lower surface 74, respectively. The keels thus project into cavities formed in the adjacent vertebral bodies 14 and 16, respectively. Preferably, the cavities define axes that are also perpendicular to the upper surface 66 and lower surface 74, respectively. In another embodiment, the keels 96 and 112 can be non-perpendicular to the upper surface 66 and lower surface 74, respectively so that the corresponding cavity for each keel also has an axis that is not perpendicular.

In another embodiment, the surfaces of keels 96 and 112 can be roughened in order that they can be securely received or anchored in the vertebral bodies. In addition, the keels can have ports or holes formed therein so that bone can grow in the ports to further strengthen the attachment of the keels to the vertebral bodies.

Another embodiment of the multi-piece implant with a selectably positionable articulating element is illustrated in FIGS. 9A through 9G. The assembled implant includes (i) a first end plate 164, which is formed from first and second upper end plate segments 164A and 164B, wherein the first end plate 164 is configured to mate with a first vertebra and (ii) a second end plate 170, which is formed from first and second lower end plate segment 170A and 170B, wherein the second end plate 170 is configured to mate with a second vertebra.

Figure 9A:
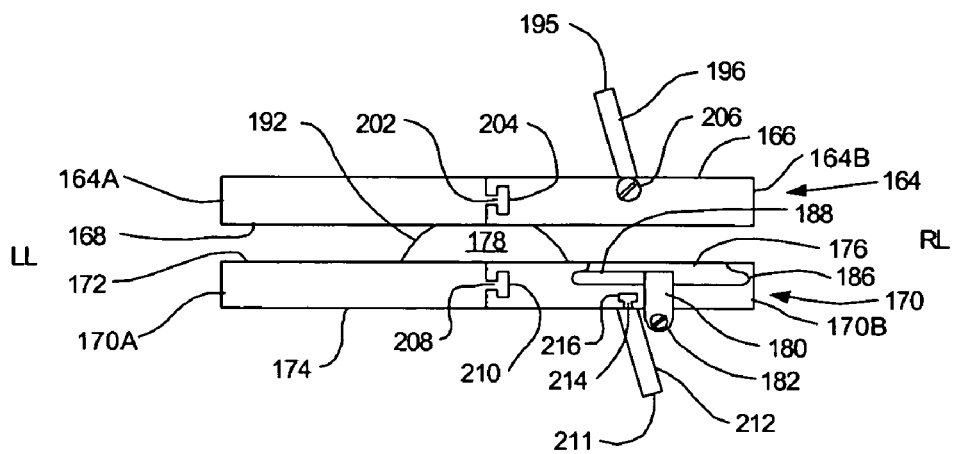
FIG. 9A is a posterior elevational partial view of an assembled multi-piece implant in its neutral position having a first or upper end plate, a second or lower end plate, and an articulating element between the first and second end plates.
Figure 9B:
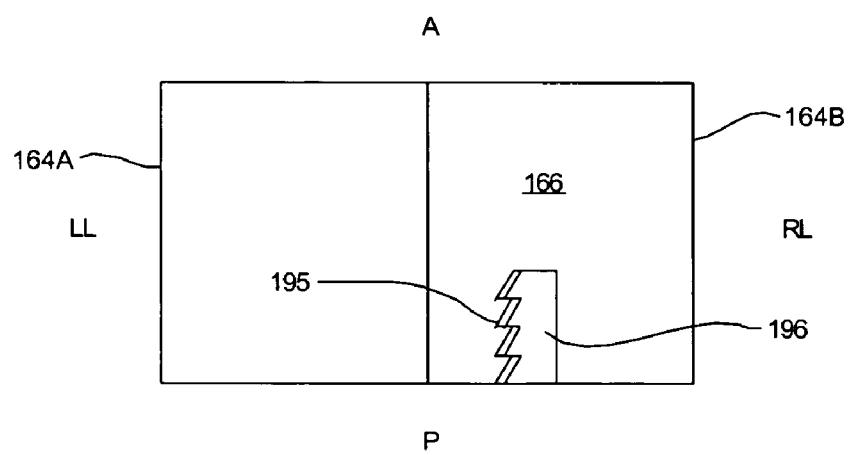
FIG. 9B is the plan view of the outer surface of the first end plate of the implant.

As shown in FIG. 9A, the first and second upper segments 164A and 164B are fixedly connected by a tongue 202 groove 204 arrangement at the sides of the two segments to form a rigid horizontal plate having an outer surface 166 that can be positioned against a first vertebra body when the implant is implanted. The first end plate 164 can be secured to the upper vertebral body with a keel 196 that has a tongue at its proximal end. The tongue fits snugly within a groove that is formed on the outer surface 166. To prevent dislodgement of the keel 196, a screw 206 is screwed into the posterior side of the first end plate 164 to secure the tongue in position. The keel 196 can have teeth 195 on its upper surface. For a posterior approach, the teeth 195 of the keel 196 would be pointed toward the posterior in order to aid in retaining the implant in place.

Similarly, the first and second lower segments 170A and 170B are fixedly connected by a tongue 208 and groove 210 arrangement at the sides of the two segments to form a rigid horizontal plate having an outer surface 174 that can be positioned against the vertebra body when the implant is implanted. The second end plate 170 can be secured to the lower vertebral body with a keel 212 that has a tongue 214 at its proximal end. The tongue fits snugly within a groove 216 that is formed on the outer surface 174 as shown in FIG. 9A. If desired, a screw can also be screwed into the posterior side of the second end plate 170 to secure the tongue 214 in position. The keel 212 can have teeth 211 on its upper surface. For a posterior approach, the teeth 211 of the keel 212 would be pointed toward the posterior in order to aid in retaining the implant in place.

Figure 9C:
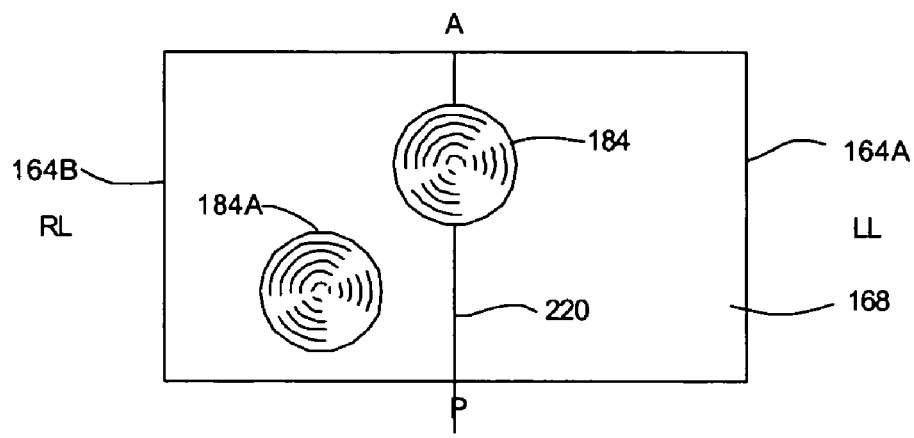
FIG. 9C is the plan view of the inner surface of the first end plate of the implant.

As shown in FIG. 9C, the second or inner surface 168 of the first end plate 164 defines recesses 184 and 184A, each with a concave surface that supports an articulating element as further explained herein. (Although only two are shown, multiple recesses preferably ranging from 2 to 4 can be employed.) As is apparent, the recess 184 is positioned along the midsaggital plane of the implant and is formed at the middle between the lateral sides of the first end plate 164. The recess 184 straddles the border 220 where the sides of the two top segments meet. Recess 184A is formed closer to the posterior surface (P) of end plate 164.

Figure 9D:
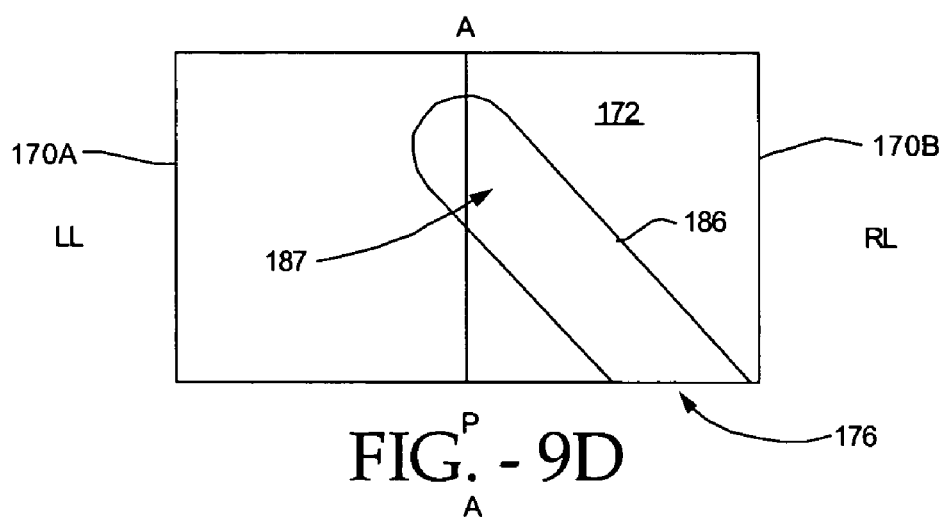
FIG. 9D is the plan view of the inner surface of the second end plate of the implant.
Figure 9E:
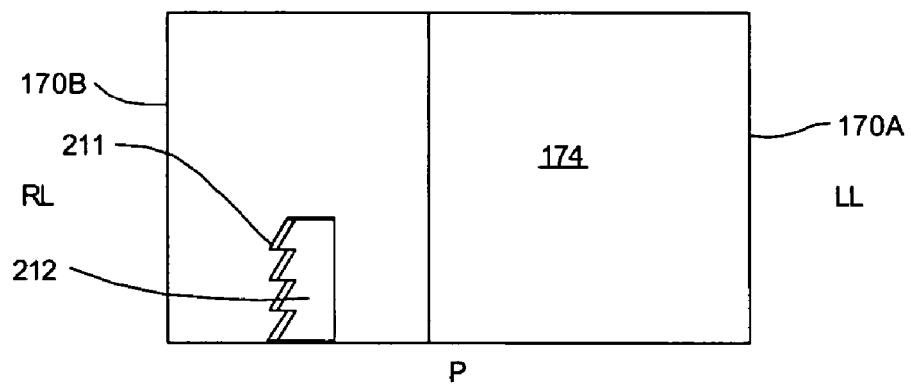
FIG. 9E is the plan view of the outer surface of the second end plate of the implant.

As shown in FIG. 9D, the second end plate 170 has a groove 186 that is formed on its inner surface 172. The groove 186 has an entrance 176 on the posterior surface of the second end plate 170 which defines a guide channel 187 that traverses the approximate width of the second end plate 170 toward the anterior surface of the second end plate 170. The axis through the center of the groove 186 is slanted relative to the sagital plane of the implant so that while the entrance 176 is located at the posterior surface of the first lower segment 170A, the groove is directed toward the center between the two segments. While each of the first and second end plates 164, 170 is illustrated has being fabricated of two segments, it is understood that either plate can comprise more than two segments, if desired.

Figure 9F:
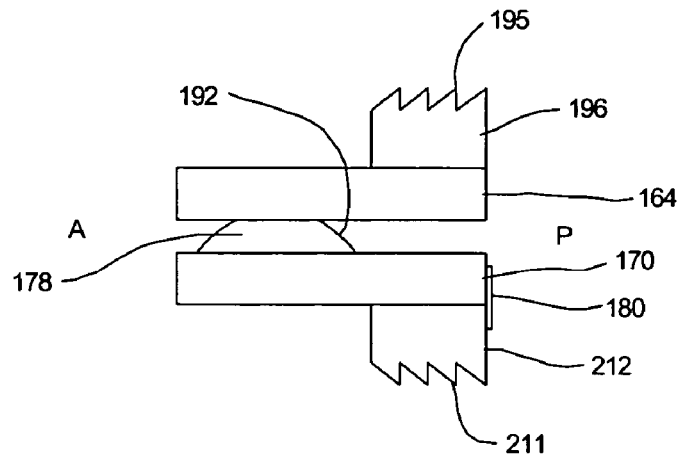
FIG. 9F is a side view of the implant.
Figure 9G:
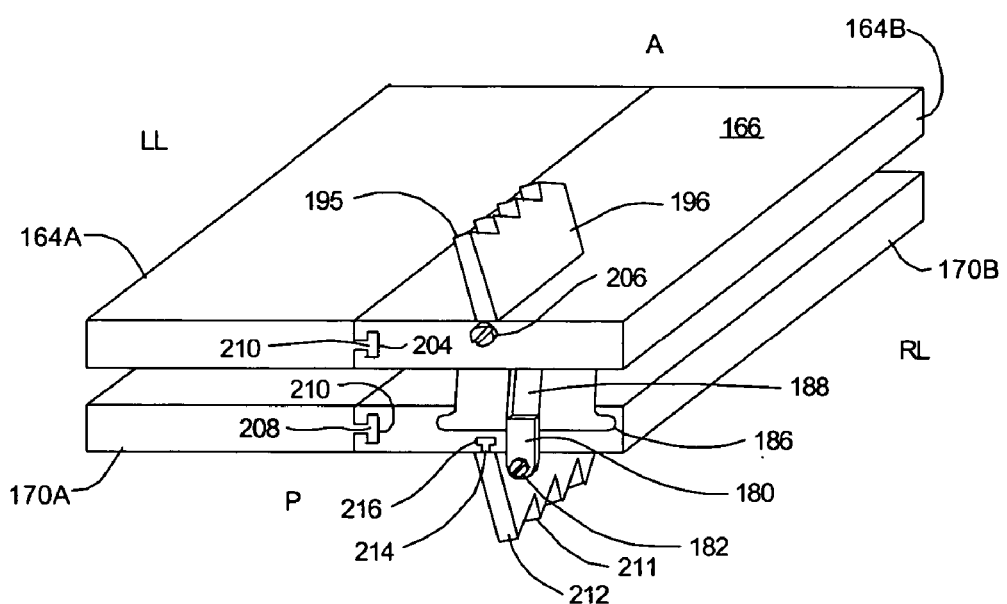
FIG. 9G is a perspective view of the assembled multi-piece implant.

As shown in FIGS. 9A, 9F, and 9G, the assembled multi-piece implant includes a third piece 178 that is positioned between the first and second end plates 164, 170. (The third piece can have the structures as shown in FIGS. 8A to 8D.) The third piece has a lower circular beveled base that fits within the groove 186 of the second end plate 170, and an upper articulating element 192 that has a convex exterior surface that substantially matches the contour of the exterior surface of the recess 184. The articulating element 192, which comes into slidable contact with the recess 184, allows the first end plate 164 and second end plate 170 to pivot and/or rotate relative to each other. The third piece 178 includes a neck 188 and strap or lip 180 at the distal end. The length of the neck 188 is designed so that once the third piece 178 is properly positioned between the first and second end plates 164, 170, the strap 180 contacts the posterior surface of second end plate 170. The third piece 178 is secured to the lower vertebral body with a screw 182 which passes through an opening on the strap 180.

The complementary configurations of the recess 184 and the exterior surface of the articulating element 192 allow the implant to simulate the natural motion of the spine. In a preferred embodiment, the articulating element 192 has a raised surface that is configured as a hemisphere and the corresponding recess 184 has a matching exterior contour shaped as a symmetrical circular cavity or concave cavity. The recess 184 covers only a portion of the surface area of the articulating element 192 at any given time. In this fashion, as the recess 184 traverses over different areas of the articulating element 192, the first end plate 164, in turn, moves relative to the second end plate 170. It is expected that the implant will restore natural movement to the patient thereby providing the patient with twisting or torsional movement as well as forward and backward bending motion, i.e., flexion and extension.

The level of movement can be tailored by appropriate design of the third piece of the multi-piece implant although it is understood the intervertebral implant functions in conjunction with the unaffected (or natural) structures of the spinal column. For example, the inter-plate distance between the first and second end plates 164 and 170, that is, the distance between inner surface 168 of the first end plate 164 and the inner surface 172 of the second end plate 170 determines the degree of forward and backward bending. The greater the inter-plate distance, the higher degree of movement possible, subject to other conditions. This inter-plate distance depends on the depth of the recess 184 and/or the height of the corresponding articulating element 192.

In assembling the multi-piece implant illustrated in FIGS. 9A through 9G, the same in situ techniques as described above involving the multi-segmented upper and lower end plates can be employed. As illustrated in FIG. 9A, the lower keel 212 is slanted relative to the plane of the second or lower plate end 170. Where the posterior approach requires that a portion of the vertebral body be removed as illustrated in FIGS. 4, 5, and 6, for example, then the slot created can be employed for supporting the keel.

Figure 10A:
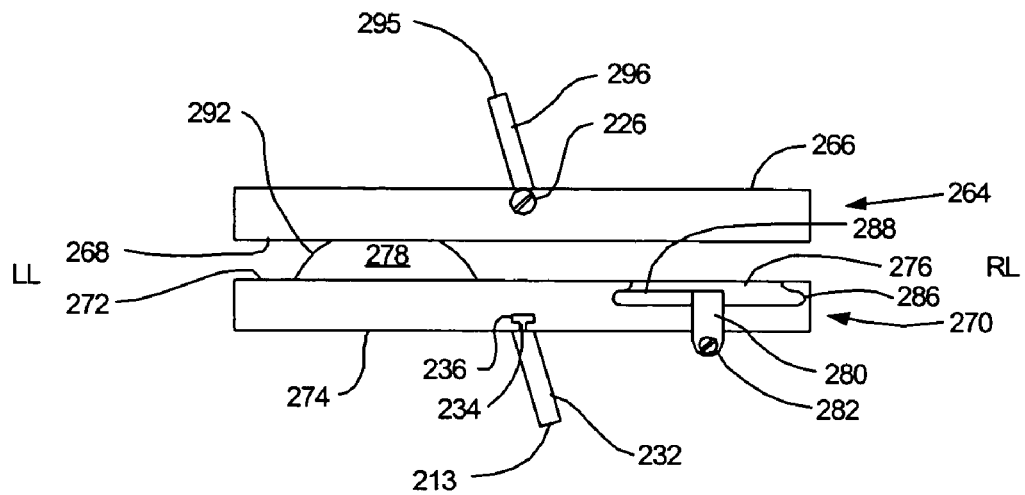
FIG. 10A is a posterior elevational partial view of an assembled multi-piece implant in its neutral position having a first or upper end plate, a second or lower end plate, and an articulating element between the first and second end plates.
Figure 10B:
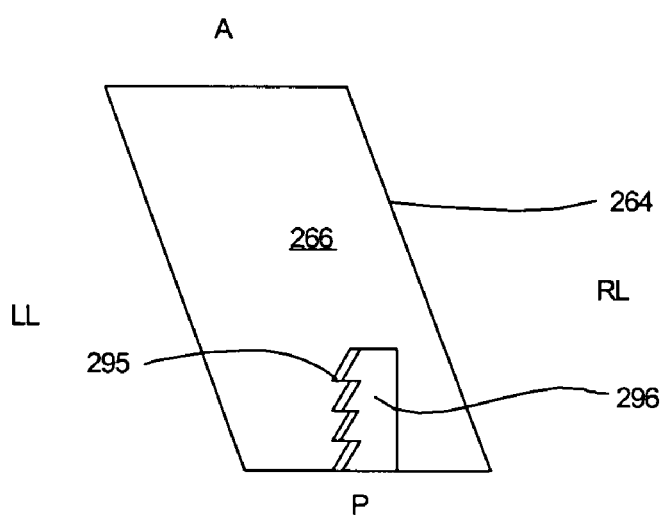
FIG. 10B is the plan view of the outer surface of the first end plate of the implant.

FIGS. 10A through 10G illustrate another embodiment of a multi-piece device that can be assembled in situ wherein the device has a selectably positionable articulating surface. (The device in FIG. 10A is shown in its neutral position where the first and second end plates have not moved relative to each other.) The assembled implant includes (i) a first end plate 264 which is configured to mate with a first vertebra and (ii) a second end plate 270 which is configured to mate with a second vertebra.

As is apparent, in this embodiment, the first and second end plates 264, 270 are configured substantially as parallelograms (both right and non-right parallelograms). As will be further described, this arrangement is particularly suited when the implant is positioned into the proximity of the center region of intervertebral space via a posterior approach whereby the implant is inserted through a side of the posterior surface of the intervertebral disk located laterally from the midsagittal plane of the intervertebral disk. Accordingly it is evident that the advantage of this embodiment is that the implant and can be inserted from one side of the spinal canal and then urged along the implant path to a position in about the center of the disk. Then the implant does not need to be urged laterally after insertion along an implant path as in other embodiments. It is understood that the implant of the present invention which includes the selectably positioning articulating element can have end plates defining other configurations.

As shown in FIG. 10A, the first end plate 264 forms a rigid horizontal member having outer surface 266 that can be positioned against the vertebra body when the implant is implanted. The first end plate 264 can be secured to the first vertebral body with a keel 296 that has a tongue at its proximal end. The tongue fits snugly within a groove that is formed on the first surface 266. To prevent dislodgement of the keel 296, a screw 226 is screwed into the posterior side of the first end plate 264 to secure the tongue in position. The keel 296 can have teeth 295 on its upper surface. For a posterior approach, the teeth 295 of the keel 296 would be pointed toward the posterior in order to aid in retaining the implant in place.

Similarly, the second end plate forms a rigid horizontal member having an outer surface 274 that can be positioned against the vertebra body when the implant is implanted. The second end plate 270 can be secured to the second vertebral body with a keel 232 that has a tongue 234 at its proximal end. The tongue fits snugly within a groove 236 that is formed on the first surface 274 as shown in FIG. 10A. If desired, a screw can also be screwed into the posterior side of the second end plate 270 to secure the tongue 234 in position. The keel 232 can have teeth 213 on its outer surface. For a posterior approach, the teeth 213 of the keel 232 would be pointed toward the posterior in order to aid in retaining the implant in place.

Figure 10C:
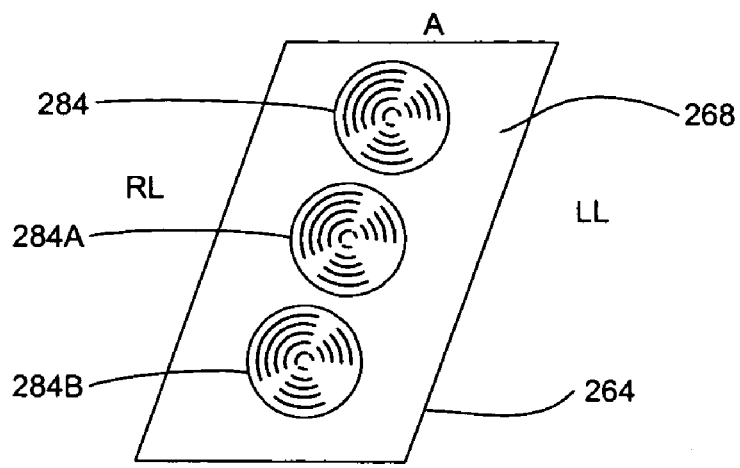
FIG. 10C is the plan view of the inner surface of the first end plate of the implant.

As shown in FIG. 10C, the second or inner lower surface 268 of the first end plate 264 defines three recesses 284, 284A and 284B that are arranged linearly. Each recess has a concave surface that can support an articulating element. Although three recesses are shown, it is understood that the implant can include multiple recesses with the number of recesses preferably ranging from 2 to 4. As further explained herein, the presence of these multiple recesses allows the surgeon to select the best location where the articulating element is to be placed. The dimensions of the three recesses can be the same or different. While each recess will have a contour matching that of the articulating element, the depth of each recess can differ. A recess that is deeper will be in contact with a greater area of the articulating element but the greater depth means that the first end plate 264 will be closer to the second end plate 270 when the implant is in its neutral position.

Figure 10D:
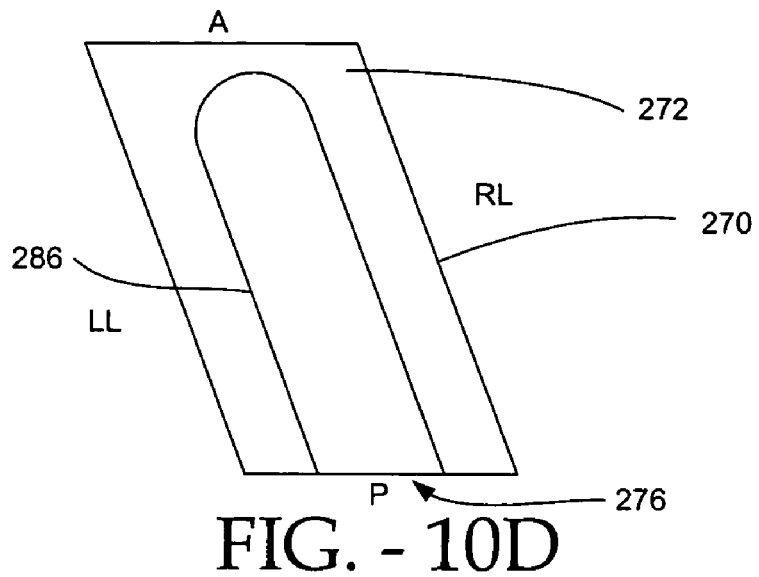
FIG. 10D is the plan view of the inner surface of the second end plate of the implant.
Figure 10E:
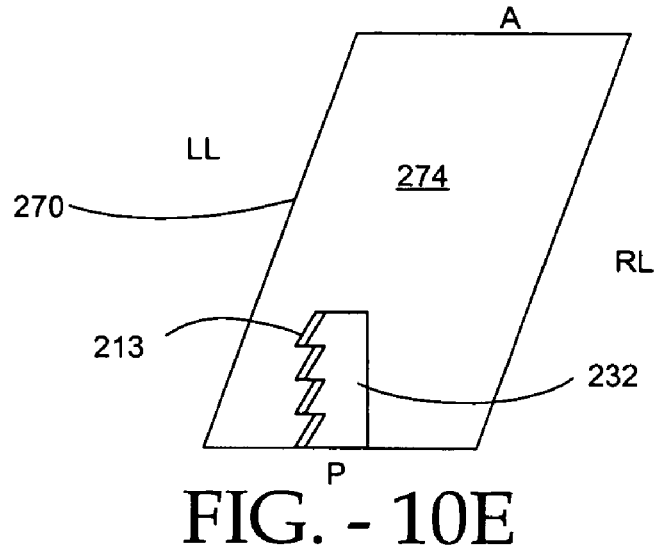
FIG. 10E is the plan view of the outer surface of the second end plate of the implant.

As shown in FIG. 10D, the second end plate 270 also has a groove 286 that is formed on its inner surface 272. The groove 286 has an entrance 276 on the posterior surface of the second end plate 270 which defines a guide channel that traverses the approximate length of the second end plate 270 toward the anterior surface of the second end plate 270. When the implant is assembled, the groove 286 faces and is aligned with the linear arrangement of the three recesses 284, 284A and 284B of the first end plate 268.

Figure 10F:
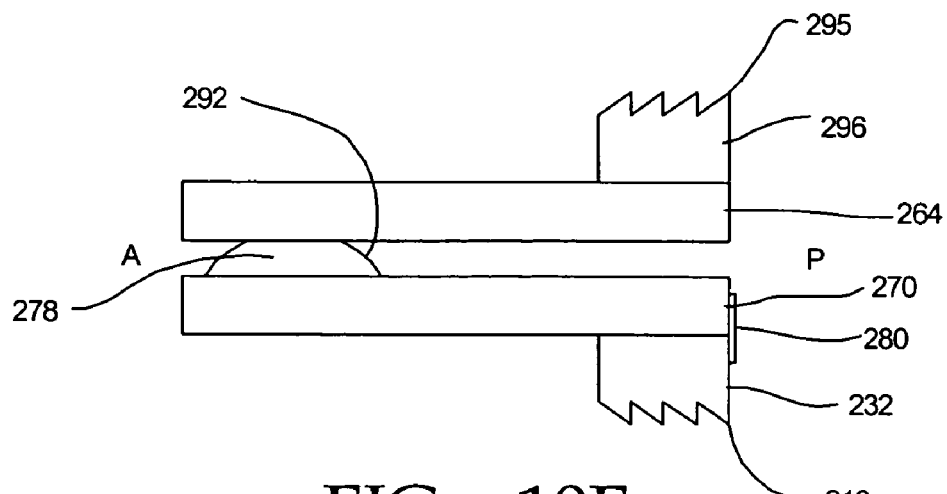
FIG. 10F is a side view of the implant.

As shown in FIGS. 10A and 10F, the assembled multi-piece implant includes a third piece 278 that is positioned between the first and second end plates 264, 270. (The third piece can have the structures as shown in FIG. 8A to 8D). The third piece has a lower circular beveled base 290 that fits within the groove 286 of the second end plate 270 and an upper articulating element 292 that has a convex exterior surface that substantially matches the contour of the exterior surface of the recess 284. The articulating element 292, which comes into slidable contact with the recess 284, allows the first end plate 264 and second end plate 270 to pivot and/or rotate relative to each other. The third piece 278 includes a neck 288 and strap or lip 280 at the distal end. The length of the neck 288 is designed so that once the third piece 278 is properly positioned between the first and second end plates 264, 270, the strap 280 contacts the posterior surface of second end plate 270. The third piece 278 is secured to the lower vertebral body with a screw 282 which passes through an opening on the strap 280.

The complementary configurations of the recess 284 and the articulating element 292 allow the implant to simulate the natural motion of the spine. In a preferred embodiment, the articulating surface 292 has a raised surface that is configured as a hemisphere and the corresponding recess 284 has a matching upper exterior contour shaped as a symmetrical circular cavity or concave cavity. The recess 284 covers only a portion of the surface area of the articulating element 292 at any given time. In this fashion, as the recess 284 traverses over different areas of the articulating element 292, the first end plate 264, in turn, moves relative to the second end plate 270. It is expected that the implant will restore natural movement to the patient thereby providing the patient with twisting or torsional movement as well as forward and backward bending motion, i.e., flexion and extension.

The level of movement can be tailored by appropriate design of the third piece of the multi-piece implant although it is understood the intervertebral implant functions in conjunction with the unaffected (or natural) structures of the spinal column. For example, the inter-plate distance between the first and second end plates 264 and 270, that is, the distance between inner surface 268 of the first end plate 264 and inner surface 272 of the second end plate 270 determines the degree of forward and backward bending. The greater the inter-plate distance, the higher degree of movement possible, subject to other conditions. This inter-plate distance depends on the depth of the recess 284 and/or the height of the corresponding articulating element 292.

In assembling the multi-piece implant in situ, the spine is exposed and the first and second end plates 264, 270 are then positioned between adjacent vertebrae by a posterior approach as described previously. Because each of the first and second end plates comprises a single integral unit, each end plate can be easily maneuvered inside the nucleus pulposis 28 through an opened annulus to a suitable position to provide maximum support for the vertebrae. As illustrated in FIG. 10H, the end plates have been positioned so that the distal end of the groove 286 is located near the center of the nucleus pulpoisis 28 at the midsigital plane of the intervertebral disk. The third piece 278 of the device can be inserted through the groove 286 and to come to rest on any of the recesses. As shown, the articulating element 292 of the third piece 278 is positioned at the distal end of the groove 286. The parallelogram configuration of the end plates allows the posterior end of the end plates to be flushed with the posterior surface of the exterior sides of the disk where part of the annulus has been removed.

It is to be understood that the embodiments of the disclosed implant can be made of medical grade titanium, stainless steel or cobalt chrome. Other materials that have appropriate structural strength and that are suitable for implantation into a patient can also be used.

Alternatively, the components of the implant can be made out of a polymer, and more specifically, the polymer is a thermoplastic. Still more specifically, the polymer is a polyketone known as polyetheretherketone (PEEK). Still more specifically, the material is PEEK 450G, which is an unfilled PEEK approved for medical implantation available from Victrex of Lancashire, Great Britain. Medical grade PEEK is available from Victrex Corporation under the product name PEEK-OPTIMA. Medical grade PEKK is available from Oxford Performance Materials under the name OXPEKK, and also from CoorsTek under the name Bio-PEKK. The components can be formed by extrusion, injection, compression molding and/or machining techniques. This material has appropriate physical and mechanical properties and is suitable for carrying and spreading the physical load between the spinous process. Further in this embodiment, the PEEK has the following additional approximate properties:

| Property | Value |
| --- | --- |
| Density | 1.3 g/cc |
| Rockwell M | 99 |
| Rockwell R | 126 |
| Tensile Strength | 97 Mpa |
| Modulus of Elasticity | 3.5 Gpa |
| Flexural Modulus | 4.1 Gpa |

It should be noted that the material selected may also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

The components can also comprised of polyetherketoneketone (PEKK). Other material that can be used include polyetherketone (PEK), polyetherketoneether-ketoneketone (PEKEKK), and polyetheretherketoneketone (PEEKK), and, generally, a polyaryletheretherketone. Further, other polyketones can be used as well as other thermoplastics.

Reference to appropriate polymers that can be used in the components can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

In operation, implant enables a forward bending movement and a rearward bending movement by sliding the upper end plate forward and backward over the articulating element relative to the lower end plate. The implant also enables a right lateral bending movement and a left lateral bending movement by sliding the lower end plate side-to-side over the articulating element relative to upper end plate. Additionally, with a loose fit between the first end plate, the second end plate and the articulating element, rotational or twisting motion along an axis that is along the spine and perpendicular to the first and second end plates is accomplished.

Figure 11:
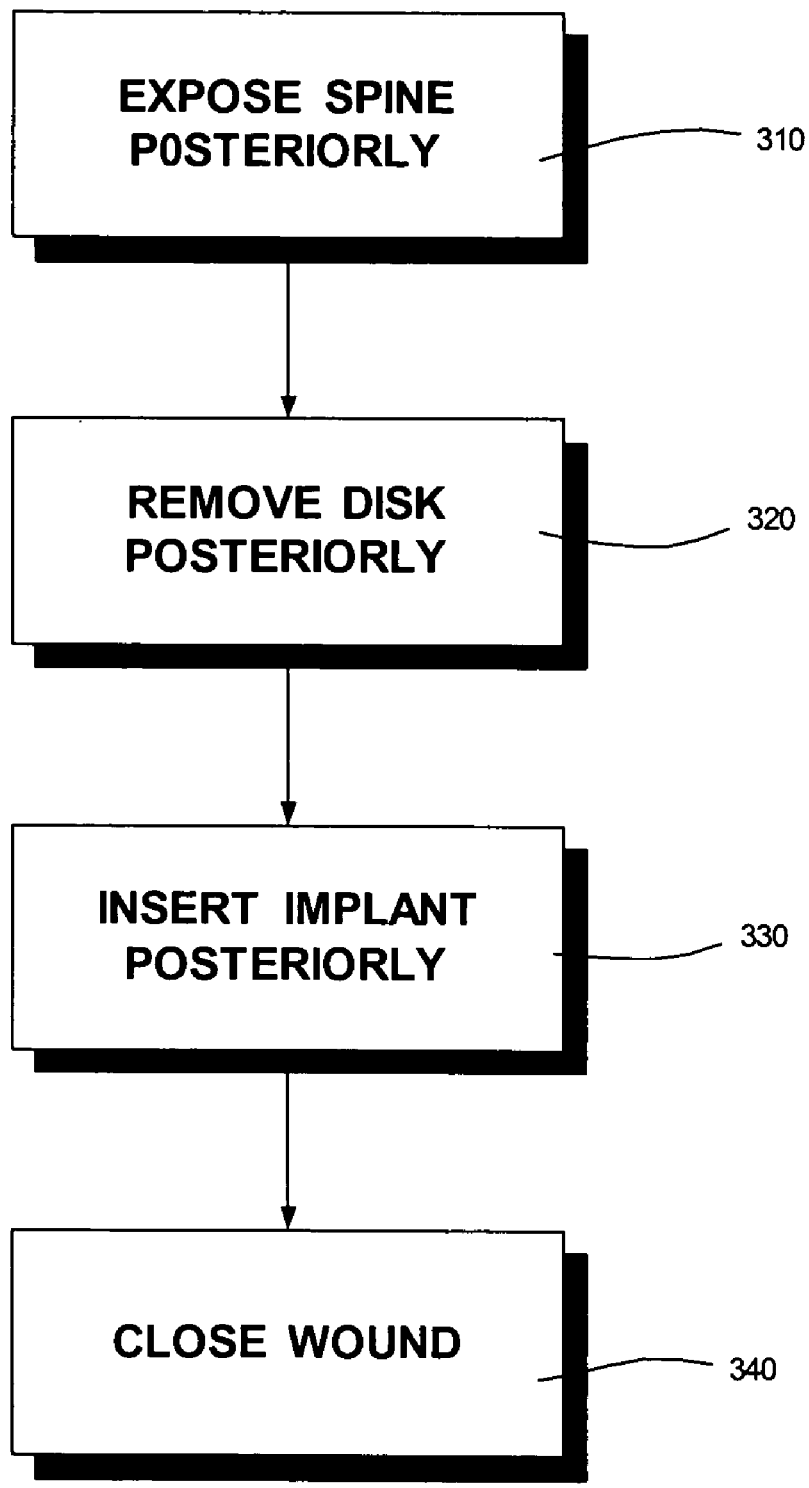
FIG. 11 is a block diagram showing the method steps of the posterior implantation of an embodiment of the disclosed implant.

FIG. 11 is a block diagram showing the basic steps of the method of inserting the implant of the present invention. First the spine is exposed through a posterior access 310, then the intervertebral disk is removed 320 if necessary. The implant is then inserted posteriorly 330 between two vertebrae and the wound is closed 340.

Additional steps, such as cutting channels into the vertebral bodies to accept the first and second keels of the first and second end plates and assembling implant by inserting the articulating element between the upper and lower end plates prior to installation can also be performed without departing from the scope of what is disclosed.

Figure 10G:
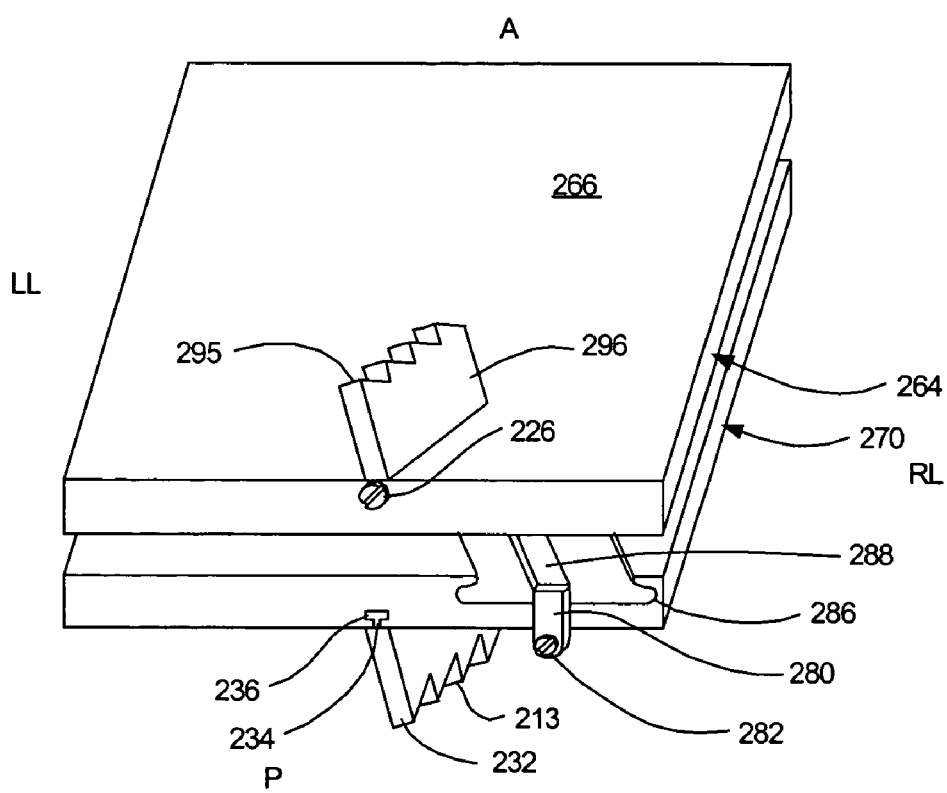
FIG. 10G is a perspective view of the assembled multi-piece implant.
Figure 10H:
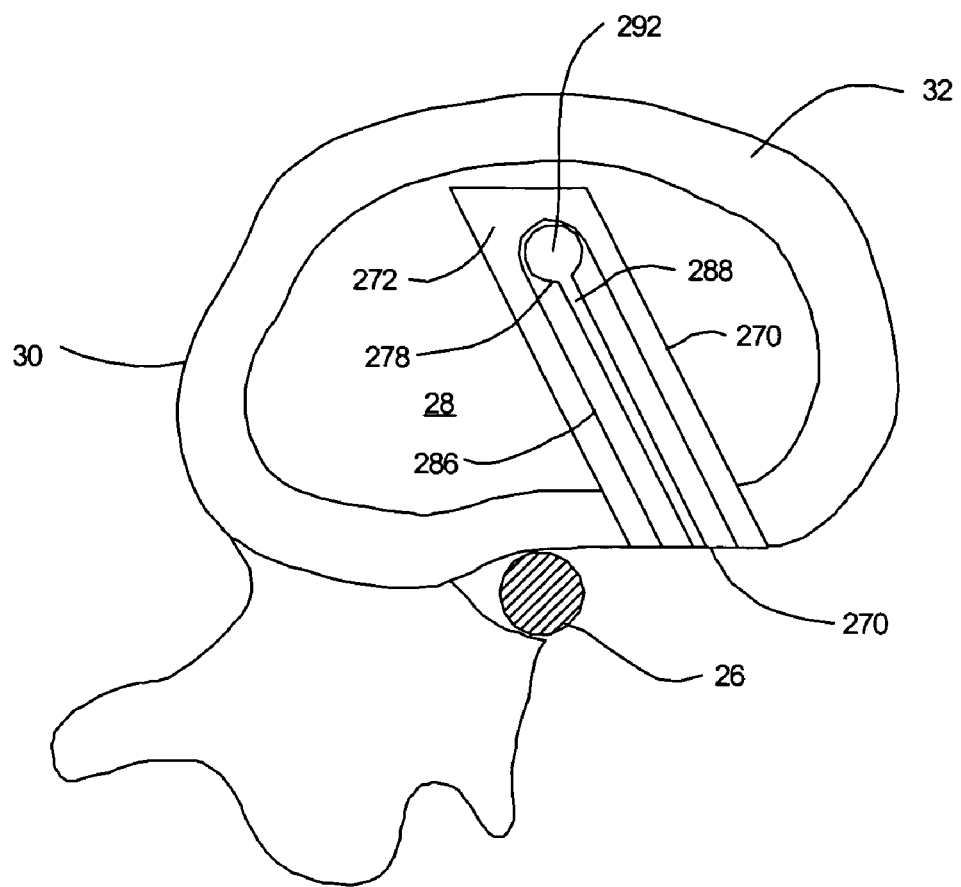
FIG. 10H shows a transaxial view of a vertebral with the lower end plate and articulating element positioned within an intervertebral space.

When the device is implanted in a slanted direction relative to the sagital axis as illustrated in FIG. 10G, the posterior surfaces of the first and second end plates along with the third piece that form the device are preferably configured so that their contours substantially match that of the posterior end of the vertebral bodies where the device is implanted. This allows the posterior side device to be flushed with the posterior surfaces of the vertebral bodies.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and their practical application, thereby enabling others skilled in the art to understand the invention and the various embodiments and with various modifications that are suited to the particular use contemplated. It is intended that the scope of the invention be defined by the following claims and their equivalence.

What is claimed:

1. A method of implanting a multiple piece device in situ between an upper and a lower vertebral body in a spine, the method comprising:
    (a) accessing an affected region of the spine posteriorly by performing a minor posterior annulotomy;
    (b) removing at least a portion of the affected region to create an exposed area in the region which is defined by a region length and a region width;
    (c) positioning a first piece of the device into the affected region, wherein the first piece comprises a first plate having a first plate length and a first plate width, with the first plate width being longer than the region length, wherein the first plate comprises two or more first segments that are joined side by side in situ and wherein the first plate is positioned so that its upper surface contacts the upper vertebral body;
    (d) positioning a second piece of the device into the affected region, wherein the second piece comprises a second plate having a second plate length and a second plate width, with the second plate width being longer than the region length, wherein the second plate comprises two or more second segments that are joined side by side in situ and wherein the second plate is positioned so that its lower surface contacts the lower vertebral body,
    wherein one of the first and second pieces comprises a groove; and
    (e) inserting a third piece of the device between the first and second pieces wherein the third piece comprises an articulating surface having a convex contour that supports one of the first plate and the second plate and a lower surface that rests on the other of the first plate and the second plate, wherein at least a portion of the convex contour is arranged to articulate relative to one of the first and second pieces and arranged to be fixed relative to the other of the first and second pieces.

2. The method of claim 1 wherein the exposed area is defined by a diagonal that is equal to or equal than either of the widths of the first and second plates and wherein:
    step (c) comprises the steps of (i) sequentially placing each of the first segments along a diagonal of the region, (ii) joining the first segments side by side to form the first plate and (iii) aligning the first plate so that its upper surface is in contact with the upper vertebral body; and
    step (d) comprises the steps of (i) sequentially placing each of the second segments along a diagonal of the region, (ii) joining the second segments side by side to form the second plate and (ii) aligning the second plate so that its lower surface is in contact with the lower vertebral body.

3. The method of claim 1 wherein the exposed area is defined by a diagonal that is shorter than at least one of the widths of the first and second segments and wherein the method comprises the steps of (i) removing a first channel from either the upper or lower vertebral body such that the first channel has an aperture on a surface of either the upper or lower vertebral body, (ii) maneuvering the first segments into the region, and (iii) maneuvering the second segments into the region.

4. The method of claim 1 wherein the exposed area is defined by a diagonal that is shorter than the widths of the first and second segments and wherein the method comprises the step of forming a first channel within either the upper or lower vertebral body such that the first channel has an aperture on a surface of either the upper or lower vertebral body and wherein
    step (c) comprises sequentially inserting the first segments into the region and into the first channel and maneuvering the first segments into the region, and
    step (d) comprises sequentially inserting the second segments into the region and into the first channel and maneuvering the second segments into region.

5. The method of claim 4 wherein the first channel defines a slot with an axis that is not perpendicular to the surface of either the upper or lower vertebral body in which the first channel is formed.

6. The method of claim 5 wherein step (c) further comprises securing the first plate to the upper vertebral body and step (d) further comprises securing the second plate to the lower vertebral body.

7. The method of claim 4 wherein step (c) further comprises securing the first plate to the upper vertebral body and step (d) further comprises securing the second plate to the lower vertebral body.

8. The method of claim 1 wherein the exposed area is defined by a diagonal that is shorter than the widths of the first and second segments, and wherein: step (c) comprises the steps of (i) forming a first channel within the upper vertebral body such that the first channel has a first aperture on a first surface of the upper vertebral body, (ii) sequentially inserting the first segments into the region and into the first channel, and (iii) maneuvering the first segments into region, and step (d) comprises the steps of (i) forming a second channel within the lower vertebral body such that the second channel has a second aperture on a second surface of the lower vertebral body, (ii) sequentially inserting the second segments into the region and into the second channel, and (iii) maneuvering the second segments into region.

9. The method of claim 8 wherein the first channel defines a slot with an axis that is not perpendicular to the surface of either the upper or lower vertebral body in which the first channel is formed.

10. The method of claim 9 wherein step (c) further comprises securing the first plate to the upper vertebral body and step (d) further comprises securing the second plate to the lower vertebral body.

11. The method of claim 8 wherein step (c) further comprises securing the first plate to the upper vertebral body and step (d) further comprises securing the second plate to the lower vertebral body.

12. The method of claim 1 wherein the articulating surface is located along a midsaggital plane between the first and second vertebral bodies.

13. A method of relieving pain associated with at least one of the spinal column and associated tissues and structures comprising the steps of:
   (a) posteriorily exposing an annulus comprised of fibrous tissue positioned between first and second adjacent vertebrae;
   (b) removing at least a portion of the fibrous tissue from the annulus; and
   (c) positioning an implant into the annulus which comprises the steps of:
      (i) inserting a first end plate having a first support surface and an outer facing surface opposite the first support surface wherein the first support surface defines two or more recesses;
      (ii) inserting a second end plate having a second support surface and an outer facing surface opposite the second support surface wherein the second support surface defines a groove;
      (iii) positioning a bearing member between the first end plate and the second end plate wherein the bearing member has (i) a convex surface that supports the first end plate and (ii) an opposite mounting surface that is in contact with the second support surface, wherein at least a portion of the mounting surface is in slidable contact with the groove and wherein the bearing member is positioned so that its convex upper surface is positioned on one of the recesses of the first support surface of the first end plate; and
      (iv) fixing the bearing member relative to the second endplate while permitting the bearing member to articulate relative to the first endplate.

14. The method of claim 13 wherein the first support surface defines a plurality of recesses and the convex surface of the bearing member is in slidable contact with one of the recesses.

15. A method of relieving pain associated with at least one of the spinal column and associated tissues and structures comprising the steps of:
   (a) posteriorily exposing an annulus comprised of fibrous tissue positioned between first and second adjacent vertebrae;
   (b) removing at least a portion of the fibrous tissue from the annulus; and
   (c) positioning an implant into the annulus which comprises the steps of:
      (i) inserting a first end plate having a first support surface and an outer facing surface opposite the first support surface wherein the first support surface defines two or more recesses;
      (ii) inserting a second end plate having a second support surface and an outer facing surface opposite the second support surface wherein the second support surface defines a groove;
      (iii) positioning a bearing member between the first end plate and the second end plate wherein the bearing member has (i) a convex surface that supports the first end plate and (ii) an opposite mounting surface that is in contact with the second support surface, wherein at least a portion of the mounting surface is in slidable contact with the groove and wherein the bearing member is positioned so that its convex upper surface is positioned on one of the recesses of the first support surface of the first end plate;
   wherein the convex surface of the bearing member is in slidable contact with one of the recesses; and
   wherein the groove defines a channel that traverses the approximate length of the second end plate and the groove has an entrance to the channel that is located on a side of the posterior end of the implant.

16. The method of claim 15 wherein the step of positioning the bearing member between the first end plate and the second end plate comprises inserting the mounting surface of the bearing member through the entrance of the groove and into the channel.

17. The method of claim 16 wherein the first end plate comprises two or more first segments that are joined side by side and wherein the second end plate comprises two or more second segments that are joined side by side.

18. The method of claim 15 wherein the channel traverses across the midsagittal plane of the implant.

19. A method of relieving pain associated with at least one of the spinal column and associated tissues and structures comprising the steps of:
   (a) posteriorly exposing an annulus of an intervertebral disk comprised of fibrous tissue positioned between first and second adjacent vertebrae;
   (b) removing at least a portion of the fibrous tissue from the annulus and creating an aperture on a side of the posterior surface of the intervertebral disk located laterally from the midsagittal plane; and
   (c) positioning an implant into the annulus which comprises the steps of:
      (i) inserting a first end plate having a first support surface and an outer surface opposite the first support surface through the aperture such that a distal end of the first end plate is located at or near the midsagittal plane between the first and second vertebrae and a proximal end of the first end plate is located adjacent the aperture;

(ii) inserting a second end plate having a second support surface and an outer surface opposite the second support surface through the aperture such that a distal end of the second end plate is located at or near the midsagittal plane between the first and second vertebrae and a proximal end of the second end plate is located adjacent the aperture wherein the second support surface includes a groove formed therein; and (iii) positioning a bearing member between the first end plate and the second end plate wherein the bearing member has (i) a convex surface that supports the first end plate and (ii) an opposite mounting surface that is in at least partial contact with the groove of the second support surface, wherein the bearing member is arranged to articulate relative to the first endplate and arranged to be fixed relative to the second endplate.

20. A method of implanting a multiple piece device in situ between an upper and a lower vertebral body in a spine, the method comprising:

(a) accessing an affected region of the spine posteriorly;

(b) removing at least a portion of the affected region to create an exposed area in the region which is defined by a region length and a region width;

(c) positioning a first piece of the device into the affected region, wherein the first piece comprises a first plate having a first plate length and a first plate width, with the first plate width being longer than the region length, wherein positioning the first piece includes (i) positioning a first segment of the first piece of the device into the affected region, and (ii) positioning a second segment of the first piece of the device into the affected region and joining the second segment to the first segment side by side in situ;

(d) positioning a second piece of the device into the affected region, wherein the second piece comprises a second plate having a second plate length and a second plate width, with the second plate width being longer than the region length, wherein positioning the second piece includes (i) positioning a first segment of the second piece of the device into the affected region, and (ii) positioning a second segment of the second piece of the device into the affected region and joining the second segment to the first segment side by side in situ; and (e) inserting a third piece of the device between the first and second pieces wherein the third piece comprises an articulating surface that supports one of the first plate and the second plate and a lower surface that rests on the other of the first plate and the second plate, wherein the third piece is arranged to articulate relative to one of the first and second pieces and arranged to be fixed relative to the other of the first and second pieces.

21. The method of claim 20 wherein the exposed area is defined by a diagonal that is equal to or equal than either of the widths of the first and second plates and wherein:

step (c) comprises the steps of (i) sequentially placing the first and second segments of the first piece along a diagonal of the region, (ii) joining the first and second segments of the first piece side by side to form the first plate and (iii) aligning the first plate so that its upper surface is in contact with the upper vertebral body; and step (d) comprises the steps of (i) sequentially placing the first ands second segments of the second piece along a diagonal of the region, (ii) joining the first and second segments of the second piece side by side to form the second plate and (ii) aligning the second plate so that its lower surface is in contact with the lower vertebral body.

22. The method of claim 20 wherein the articulating surface has a convex contour and the first plate has a groove and at least a portion of the convex contour is in slidable contact with a groove surface.

23. The method of claim 20 wherein the exposed area is defined by a diagonal that is shorter than the widths of the first and second segments of the first and second pieces and wherein the method comprises the step of forming a first channel within either the upper or lower vertebral body such that the first channel has an aperture on a surface of either the upper or lower vertebral body and wherein step (c) comprises sequentially inserting the first segments into the region and into the first channel and maneuvering the first segments into the region, and step (d) comprises sequentially inserting the second segments into the region and into the first channel and maneuvering the second segments into region.

24. A method of relieving pain associated with at least one of the spinal column and associated tissues and structures comprising the steps of:

(a) posteriorily exposing an annulus comprised of fibrous tissue positioned between first and second adjacent vertebrae;

(b) removing at least a portion of the fibrous tissue from the annulus; and (c) positioning an implant into the annulus which comprises the steps of:

(i) inserting a first end plate having a first support surface and an outer facing surface opposite the first support surface, wherein the first support surface includes two or more recesses formed therein;

(ii) inserting a second end plate having a second support surface and an outer facing surface opposite the second support surface;

(iii) determining which of the two or more recesses is formed in a location most conducive to providing a desired articulation; and (iv) positioning a bearing member in situ between the first end plate and the second end plate so that a convex surface of the bearing member is positioned within the determined recess.

25. The method of claim 24 wherein the first support surface defines a plurality of recesses and the second support surface defines a groove into which the mounting surface of the bearing member is positioned and the convex surface of the bearing member is in slidable contact with one of the recesses.

26. The method of claim 25 wherein the groove defines a channel that traverses the approximate length of the second end plate and the groove has an entrance to the channel that is located on a side of the posterior end of the implant.

* * * * *